(12) United States Patent
Howell et al.

(10) Patent No.: US 11,727,558 B2
(45) Date of Patent: Aug. 15, 2023

(54) METHODS AND APPARATUSES FOR COLLECTION AND VISUALIZATION OF ULTRASOUND DATA

(71) Applicant: BFLY OPERATIONS, INC., Burlington, MA (US)

(72) Inventors: Audrey Howell, Brooklyn, NY (US); Matthew de Jonge, Brooklyn, NY (US); Kurt Guenther, Burlington, MA (US); Abraham Neben, Guilford, CT (US); Tomer Gafner, Forest Hills, NY (US); Yang Liu, Hoboken, NJ (US); Nathan Silberman, Brooklyn, NY (US); Cristina Shin, San Francisco, CA (US); Swaminathan Sankaranarayanan, Guilford, CT (US)

(73) Assignee: BFLY OPERATIONS, INC., Burlington, MA (US)

( * ) Notice: Subject to any disclaimer, the term of this patent is extended or adjusted under 35 U.S.C. 154(b) by 417 days.

(21) Appl. No.: 16/838,986

(22) Filed: Apr. 2, 2020

(65) Prior Publication Data
US 2020/0320694 A1 Oct. 8, 2020

Related U.S. Application Data

(60) Provisional application No. 62/828,959, filed on Apr. 3, 2019.

(51) Int. Cl.
*G06K 9/00* (2022.01)
*G06T 7/00* (2017.01)
(Continued)

(52) U.S. Cl.
CPC ............ *G06T 7/0012* (2013.01); *A61B 8/085* (2013.01); *A61B 8/462* (2013.01); *A61B 8/466* (2013.01);
(Continued)

(58) Field of Classification Search
CPC ..... G06T 7/0012; G06T 15/005; G06T 19/20; G06T 2200/24; G06T 2207/10136;
(Continued)

(56) References Cited

U.S. PATENT DOCUMENTS 9,629,615 B1 * 4/2017 Tavakoli .............. A61B 8/5246
9,911,062 B1 * 3/2018 Ahmad ..................... G06T 7/73
(Continued)

FOREIGN PATENT DOCUMENTS

WO WO-2015049609 A1 * 4/2015 ............... A61B 5/14

OTHER PUBLICATIONS

International Preliminary Report on Patentability for International Application No. PCT/US2020/026460, dated Oct. 14, 2021.
(Continued)

*Primary Examiner* — Tom Y Lu
(74) *Attorney, Agent, or Firm* — Osha Bergman Watanabe & Burton LLP

(57) ABSTRACT

Some aspects of the technology described herein relate to configuring an ultrasound device to perform a three-dimensional ultrasound imaging sweep, and displaying ultrasound images and segmented portions of the ultrasound images as the ultrasound images are collected during the three-dimensional ultrasound imaging sweep. Certain aspects relate to displaying an ultrasound image collected by an ultrasound device and configuring the ultrasound device to perform a three-dimensional ultrasound imaging sweep based on the ultrasound image collected by the ultrasound device.

17 Claims, 24 Drawing Sheets

(51) Int. Cl.
*A61B 8/00* (2006.01)
*A61B 8/08* (2006.01)
*G06T 19/20* (2011.01)
*G06T 15/00* (2011.01)

(52) U.S. Cl.
CPC .............. *A61B 8/483* (2013.01); *A61B 8/523* (2013.01); *G06T 15/005* (2013.01); *G06T 19/20* (2013.01); *G06T 2200/24* (2013.01); *G06T 2207/10136* (2013.01); *G06T 2207/30092* (2013.01); *G06T 2219/2016* (2013.01)

(58) Field of Classification Search
CPC ... G06T 2207/30092; G06T 2219/2016; G06T 2210/41; G06T 19/00; A61B 8/085; A61B 8/462; A61B 8/466; A61B 8/483; A61B 8/523; A61B 8/463; A61B 8/467; A61B 8/5223
See application file for complete search history.

(56) References Cited

U.S. PATENT DOCUMENTS

| | | | |
|---|---|---|---|
| 10,628,932 | B2 | 4/2020 | Rothberg et al. |
| 10,702,242 | B2 | 7/2020 | de Jonge et al. |
| 10,706,520 | B2 | 7/2020 | Rothberg et al. |
| 10,709,415 | B2 | 7/2020 | Neben et al. |
| 2009/0264757 | A1 | 10/2009 | Yang et al. |
| 2011/0004101 | A1 | 1/2011 | Yang et al. |
| 2011/0055447 | A1 | 3/2011 | Costa |
| 2012/0004545 | A1 | 1/2012 | Ziv-Ari et al. |
| 2013/0016092 | A1 | 1/2013 | Collins et al. |
| 2016/0228091 | A1 | 8/2016 | Chiang et al. |
| 2017/0329927 | A1* | 11/2017 | Taherian .................. A61B 6/50 |
| 2017/0360397 | A1 | 12/2017 | Rothberg et al. |
| 2017/0360401 | A1 | 12/2017 | Rothberg et al. |
| 2017/0360402 | A1 | 12/2017 | de Jonge et al. |
| 2017/0360403 | A1 | 12/2017 | Rothberg et al. |
| 2017/0360404 | A1 | 12/2017 | Gafner et al. |
| 2017/0360411 | A1 | 12/2017 | Rothberg et al. |
| 2017/0360412 | A1 | 12/2017 | Rothberg et al. |
| 2018/0085043 | A1* | 3/2018 | Panicker ................ A61B 5/204 |
| 2018/0146953 | A1* | 5/2018 | Jaremko ................ G06T 17/20 |
| 2018/0214122 | A1 | 8/2018 | Ansell et al. |
| 2018/0333140 | A1* | 11/2018 | Wodlinger ............ A61B 8/085 |
| 2019/0130554 | A1 | 5/2019 | Rothberg et al. |
| 2019/0142388 | A1 | 5/2019 | Gonyeau et al. |
| 2019/0196600 | A1 | 6/2019 | Rothberg et al. |
| 2019/0261957 | A1 | 8/2019 | Zaslavsky et al. |
| 2019/0266716 | A1 | 8/2019 | Rothberg et al. |
| 2019/0282208 | A1 | 9/2019 | Silberman et al. |
| 2019/0307428 | A1 | 10/2019 | Silberman et al. |
| 2020/0037986 | A1 | 2/2020 | Silberman et al. |
| 2020/0037987 | A1 | 2/2020 | Silberman et al. |
| 2020/0037998 | A1 | 2/2020 | Gafner et al. |
| 2020/0046314 | A1 | 2/2020 | Neben et al. |
| 2020/0046322 | A1 | 2/2020 | Silberman |
| 2020/0054307 | A1 | 2/2020 | Silberman et al. |
| 2020/0060658 | A1 | 2/2020 | Gafner et al. |
| 2020/0129151 | A1 | 4/2020 | Neben et al. |
| 2020/0155113 | A1 | 5/2020 | Neben et al. |
| 2020/0211174 | A1 | 7/2020 | Rothberg et al. |
| 2020/0214672 | A1 | 7/2020 | de Jonge et al. |
| 2020/0214674 | A1 | 7/2020 | Gafner et al. |
| 2020/0214679 | A1 | 7/2020 | Silberman et al. |

OTHER PUBLICATIONS

PCT/US2020/026460, Jun. 26, 2020, International Search Report and Written Opinion.

International Search Report and Written Opinion dated Jun. 26, 2020 in connection with International Application No. PCT/US2020/026460.

Supplementary European Search Report issued in corresponding application No. EP20783589 dated Nov. 25, 2022 (8 pages).

* cited by examiner

METHODS AND APPARATUSES FOR COLLECTION AND VISUALIZATION OF ULTRASOUND DATA

CROSS-REFERENCE TO RELATED APPLICATIONS

The present application claims the benefit under 35 U.S.C. § 119(e) of U.S. Patent Application Ser. No. 62/828,959, filed Apr. 3, 2019, and entitled "METHODS AND APPARATUSES FOR COLLECTION AND VISUALIZATION OF ULTRASOUND DATA," which is hereby incorporated herein by reference in its entirety.

FIELD

Generally, the aspects of the technology described herein relate to collection of ultrasound images.

BACKGROUND

Ultrasound probes may be used to perform diagnostic imaging and/or treatment, using sound waves with frequencies that are higher than those audible to humans. Ultrasound imaging may be used to see internal soft tissue body structures. When pulses of ultrasound are transmitted into tissue, sound waves of different amplitudes may be reflected back towards the probe at different tissue interfaces. These reflected sound waves may then be recorded and displayed as an image to the operator. The strength (amplitude) of the sound signal and the time it takes for the wave to travel through the body may provide information used to produce the ultrasound image. Many different types of images can be formed using ultrasound devices. For example, images can be generated that show two-dimensional cross-sections of tissue, blood flow, motion of tissue over time, the location of blood, the presence of specific molecules, the stiffness of tissue, or the anatomy of a three-dimensional region.

SUMMARY

According to an aspect of the present application, an apparatus is provided, comprising a processing device in operative communication with an ultrasound device. The processing device is configured to: display an initial ultrasound image collected by the ultrasound device; configure the ultrasound device to perform a three-dimensional ultrasound imaging sweep based on the initial ultrasound image collected by the ultrasound device; display ultrasound images as the ultrasound images are collected during the three-dimensional ultrasound imaging sweep; display a cine including the ultrasound images and segmented portions of the ultrasound images that were collected during the three-dimensional ultrasound imaging sweep; and display a three-dimensional visualization based on the segmented portions of the ultrasound images that were collected during the three-dimensional ultrasound imaging sweep.

Some aspects include at least one non-transitory computer-readable storage medium storing processor-executable instructions that, when executed by at least one processor, cause the at least one processor to perform the above aspects and embodiments. Some aspects include a method to perform the actions that the processing device is configured to perform.

BRIEF DESCRIPTION OF THE DRAWINGS

Various aspects and embodiments will be described with reference to the following exemplary and non-limiting figures. It should be appreciated that the figures are not necessarily drawn to scale. Items appearing in multiple figures are indicated by the same or a similar reference number in all the figures in which they appear.

DETAILED DESCRIPTION

Figure 1:
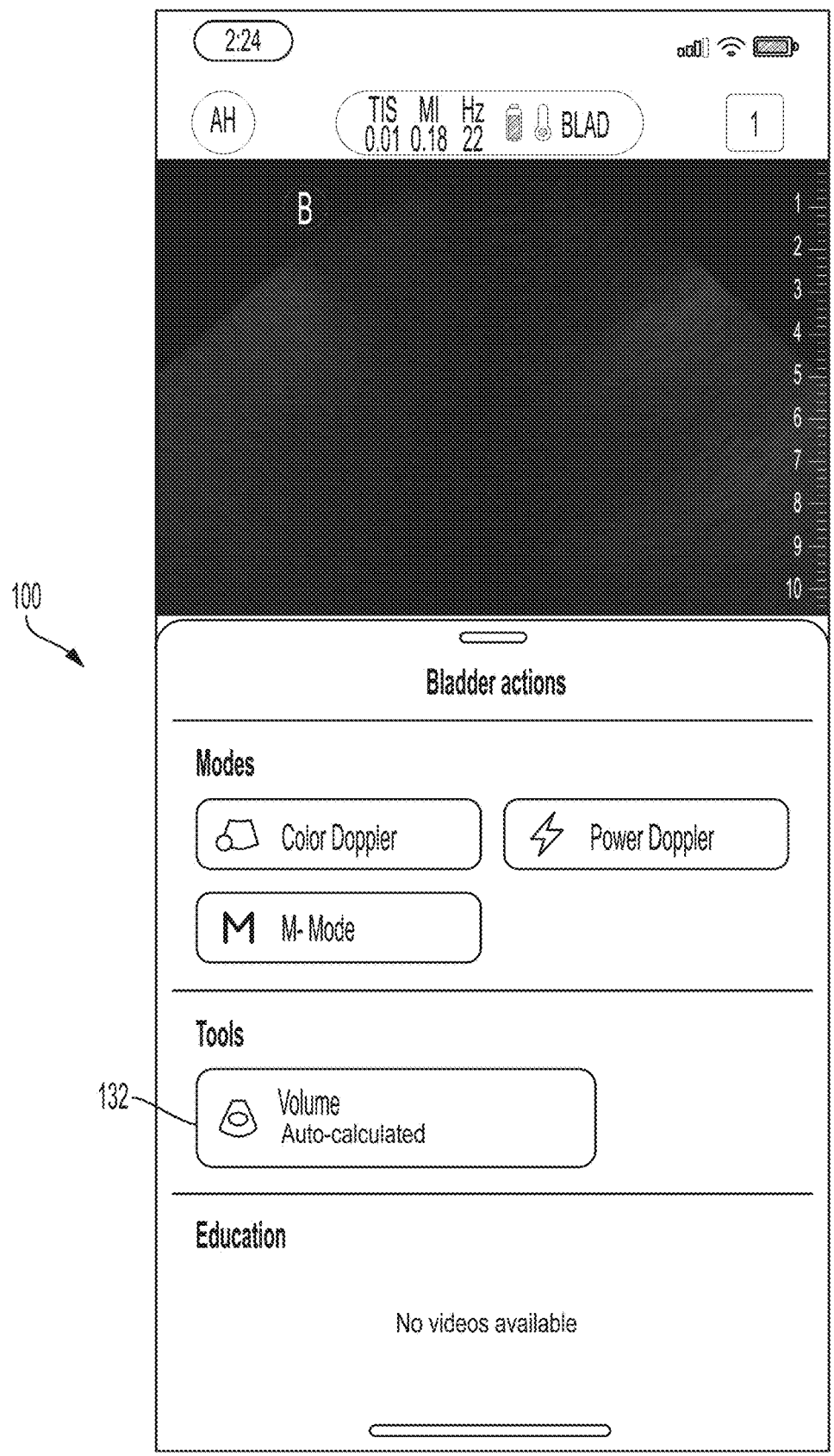
FIG. 1 illustrates an example graphical user interface (GUI), according to a non-limiting embodiment of the present application.

Some applications of ultrasound imaging include capturing one or more ultrasound images of an anatomical structure (e.g., a bladder) with an ultrasound device and performing a clinical measurement based on the ultrasound images. In some embodiments, capturing the ultrasound images may include performing a three-dimensional (3D) ultrasound imaging sweep with the ultrasound device. The measurement may be based on segmented portions of the ultrasound images. For example, measurement of bladder volume may be based on segmented portions of ultrasound images that represent the interior of the bladder depicted in the ultrasound images. The inventors have recognized that prior to performing such a 3D sweep, it may be helpful to display an ultrasound image collected by an ultrasound device at one of the locations along the 3D sweep and to display a segmented portion of this ultrasound image. Using this segmented portion as an example, the user may be able to determine whether segmented portions of ultrasound images collected during the 3D sweep may be usable for the measurement. If they may be usable, then the user may initiate the 3D sweep. If they may not be usable, then the user may reposition the ultrasound device. The inventors have also recognized that after the 3D sweep, it may be helpful to display ultrasound images and segmented portions of the ultrasound images that were collected during the 3D sweep. Based on viewing the segmented portions that were collected, the user may determine whether the segmented portions of ultrasound images collected during the 3D sweep may be usable for the measurement. If they may be usable, then the user may use the measurement value produced based on the 3D sweep. If they may not be usable, then the user may reposition the ultrasound device and initiate another 3D sweep. The inventors have also recognized that after the 3D sweep, it may be helpful to display, based on the segmented portions of the ultrasound images collected during the 3D sweep, a 3D visualization of the anatomical structure that is being measured (e.g., a 3D visualization of the bladder whose volume is being measured). Based on viewing the 3D visualization of the anatomical structure, the user may determine whether the ultrasound images and segmented portions of ultrasound images collected during the 3D sweep may be usable for the measurement. If they may be usable, then the user may use the measurement value produced based on the 3D sweep. If they may not be usable, then the user may reposition the ultrasound device and initiate another 3D sweep.

It should be appreciated that the embodiments described herein may be implemented in any of numerous ways. Examples of specific implementations are provided below for illustrative purposes only. It should be appreciated that these embodiments and the features/capabilities provided may be used individually, all together, or in any combination of two or more, as aspects of the technology described herein are not limited in this respect.

FIGS. 1-22 illustrate graphical user interfaces (GUI) that are displayed by a processing device. The processing device may be, for example, a handheld device such as a mobile phone or tablet, or a laptop. The processing device may be in operative communication with an ultrasound device. The ultrasound device and the processing device may communicate over a wired communication link (e.g., over Ethernet, a Universal Serial Bus (USB) cable or a Lightning cable) or over a wireless communication link (e.g., over a BLUETOOTH, WiFi, or ZIGBEE wireless communication link). In some embodiments, the GUIs may be displayed on a touch-sensitive display screen of the processing device.

FIG. 1 illustrates an example GUI 100, in accordance with certain embodiments described herein. The GUI 100 includes a volume auto-calculation option 132. In some embodiments, upon receiving a selection of the volume auto-calculation option 132, the processing device may display the GUI 200.

Figure 2:
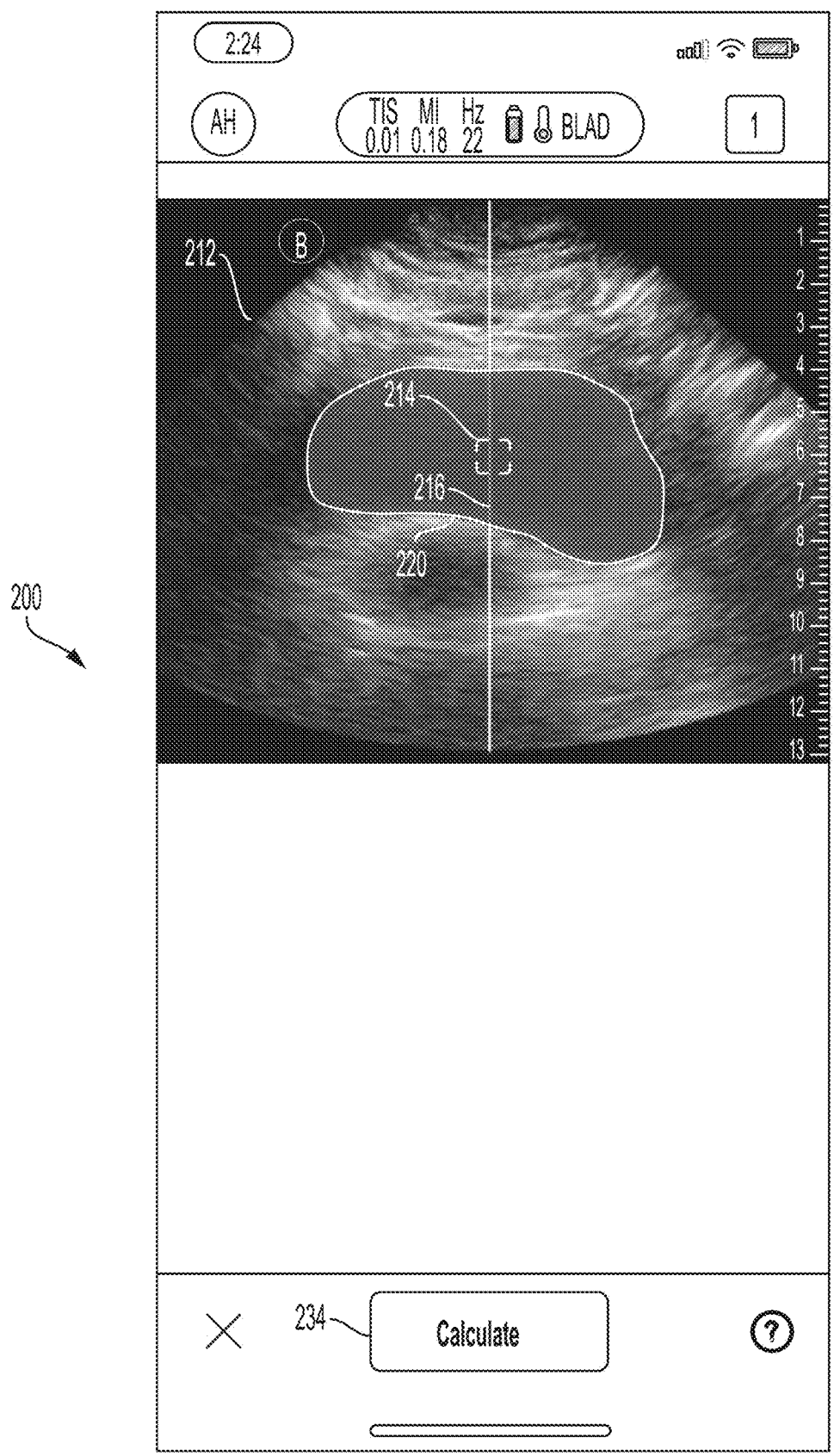
FIG. 2 illustrates an alternative GUI, according to another non-limiting embodiment of the present application.

FIG. 2 illustrates another example GUI 200, in accordance with certain embodiments described herein. The GUI 200 includes an ultrasound image 212, a segmented portion 220, a calculate option 234, a symbol 214, and a vertical line 216. The ultrasound image 212 may be generated based on raw ultrasound data collected by the ultrasound device. In some embodiments, the ultrasound device may generate the ultrasound image 212 based on the raw ultrasound data and the processing device may receive the ultrasound image 212 from the ultrasound device and display it. In some embodiments, the ultrasound device may generate scan lines from the raw ultrasound data, and the processing device may receive the scan lines from the ultrasound device and generate the ultrasound image 212 based on the scan lines. In some embodiments, the processing device may receive the raw ultrasound data from the ultrasound device and generate the ultrasound image 212 based on the raw ultrasound data. The ultrasound image 212 and the segmented portion 220 displayed in the GUI 200 may be updated as new ultrasound data is collected. (Ultrasound images described further herein may be generated in the same manner as described with reference to the ultrasound image 212.)

The symbol 214 is superimposed on the ultrasound image 212 and may be an indicator of the location of a specific point on the bladder. In FIG. 2, the symbol 214 is an indicator of the location of the centroid of the bladder. The vertical line 216 extends vertically (with respect to the ultrasound image 212) through the ultrasound image 212 and is located halfway along the horizontal dimension of the ultrasound image 212. The location of the symbol 214 may be updated as new ultrasound images 212 are collected and displayed. The symbol 214 and the vertical line 216 may help the user in centering the bladder in the ultrasound image 212.

In FIG. 2, the segmented portion 220 represents the interior of the bladder as depicted in the ultrasound image 212. In some embodiments, the processing device may use a statistical model to generate the segmented portion 220. In particular, the statistical model may be trained to determine the location for segmented portions in ultrasound images. For example, a statistical model may be trained to determine the location of the interior of bladders as depicted in ultrasound images. The statistical model may be stored on the processing device or stored on another electronic device (e.g., a server) and accessed by the processing device. In some embodiments, the statistical model may be trained on multiple pairs of input and output training data sets as a segmentation model. Each set of input training data may be an ultrasound image depicting a bladder. Each set of output training data may be a segmentation mask that is an array of values equal in size to the input training data ultrasound image, and pixels corresponding to locations within the bladder in the ultrasound image are manually set to 1 and other pixels are set to 0. Based on this training data, the statistical model may learn to output, based on an inputted ultrasound image (e.g., the ultrasound image 212), a segmentation mask where each pixel has a value representing the probability that the pixel corresponds to a location within the bladder in the ultrasound image (values closer to 1) or outside the anatomical structure (values closer to 0). The processing device may select all pixels in the segmentation mask that have a value greater than a threshold value (e.g., 0.5) as being within the bladder and highlight these pixels in the ultrasound image 212 to display the segmented portion 220. Other aspects of an ultrasound image (e.g., a boundary, a diameter, etc.) may be segmented in the same manner. The statistical model may be, for example, a convolutional neural network, a fully connected neural network, a recurrent neural network (e.g., a long short-term memory (LSTM) recurrent neural network), a random forest, a support vector machine, a linear classifier, and/or any other statistical model, and may use deep learning techniques to generate the segmented portion 220. (Segmented portions described further herein may be generated in the same manner as described with reference to the segmented portion 220.)

In some embodiments, upon receiving a selection of the calculate option 234, the processing device may configure the ultrasound device to perform a 3D sweep, and display the GUI 300. A user may decide to select the calculate option 234 once the bladder is properly positioned in the ultrasound image 212 as displayed in the GUI 200. For example, the user may decide to select the calculate option 234 once the bladder is centered in the ultrasound image 212, and may use the symbol 214 and the vertical line 216 to determine when the bladder is centered in the ultrasound image 212.

The 3D sweep may be an elevational sweep. In other words, during the 3D sweep, the ultrasound device may collect multiple ultrasound images, each ultrasound image collected along a different imaging slice at a different angle along the elevational dimension of the ultrasound device's transducer array. The processing device may configure the ultrasound device and/or itself to use beamforming to focus an ultrasound beam along a different direction at each stage of the 3D sweep. The 3D sweep may be performed while the user maintains the ultrasound device at the same position and orientation it was at when the ultrasound device collected the ultrasound image 212. The ultrasound device may use a two-dimensional array of ultrasound transducers on a chip to perform the three-dimensional ultrasound imaging sweep while the user maintains the ultrasound device at the same position and orientation it was at when the ultrasound device collected the ultrasound image 212. Further description of such a chip may be found with reference to FIG. 24. The beamforming process may include applying different delays to the transmitted and received ultrasound waves/data from different portions of the ultrasound transducer array (e.g., different delays for different elevational rows, where a row refer to a sequence of elements at the same position on the short axis of the ultrasound transducer array). The delays may be applied by the ultrasound device and/or by the processing device when processing the resulting data. The processing device may configure the ultrasound device to perform the 3D sweep based on the ultrasound image 212 that was collected prior to selection of the calculate option 234. In some embodiments, the imaging slice of the ultrasound image 212 may be the center imaging slice of the 3D sweep. In some embodiments, the imaging slice of the ultrasound image 212 may be one extreme of the 3D sweep.

Figure 3:
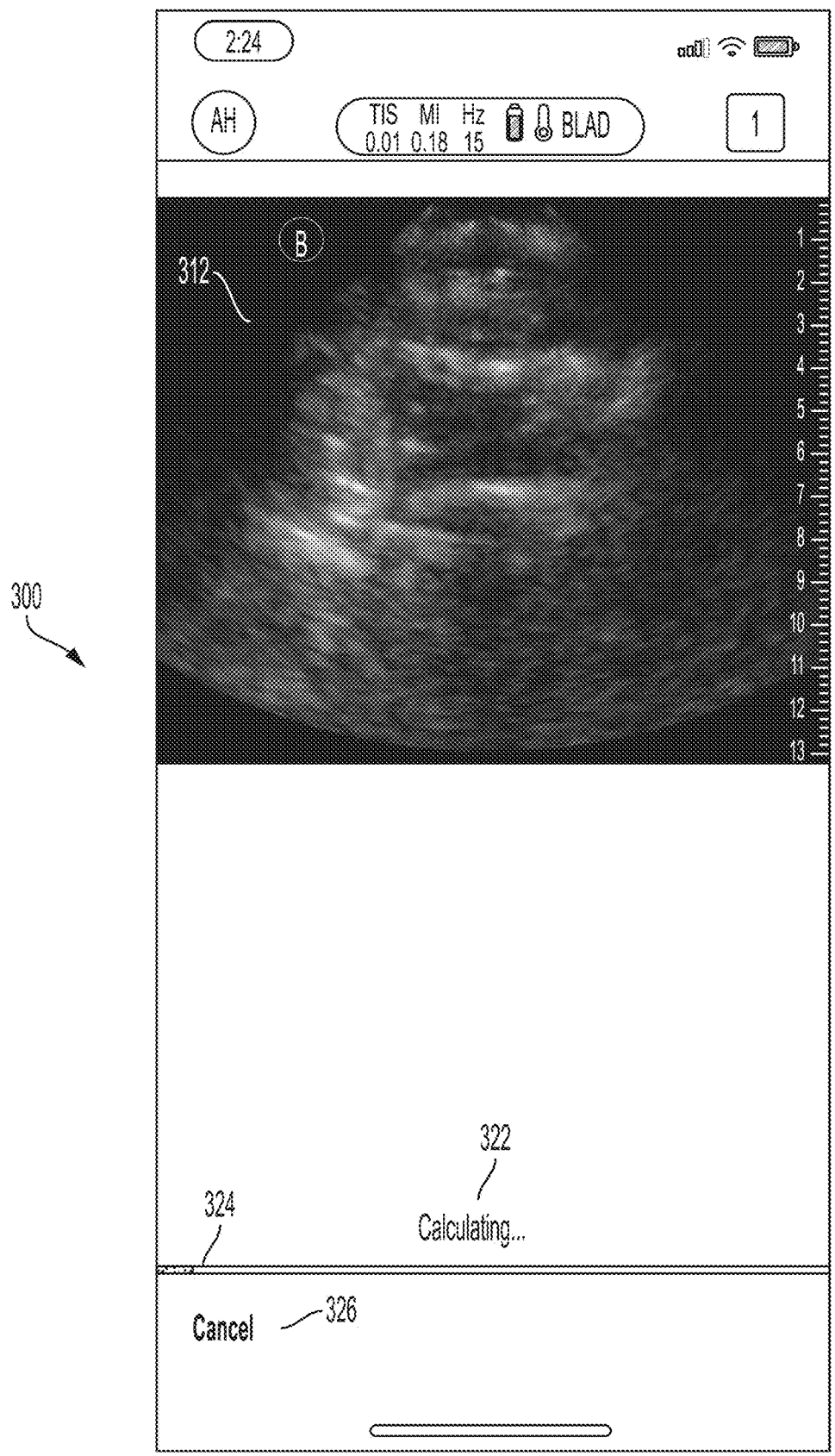
FIG. 3 illustrates another example GUI, in accordance with certain embodiments described herein.

FIG. 3 illustrates another example GUI 300, in accordance with certain embodiments described herein. The GUI 300 includes an ultrasound image 312, a calculation indicator 322, a calculation time indicator 324, and a cancel option 326. The ultrasound image 312 may be the ultrasound images most recently collected during the sweep. In some embodiments, the calculation indicator 322 may indicate that the processing device is presently recording ultrasound images (including the ultrasound image 312) for use in calculation. In some embodiments, the calculation time indicator 324 may indicate how much time has elapsed and how much time remains in the 3D sweep. In some embodiments, upon determining an activation of the cancel option 326, the processing device may stop the 3D sweep.

Figure 4:
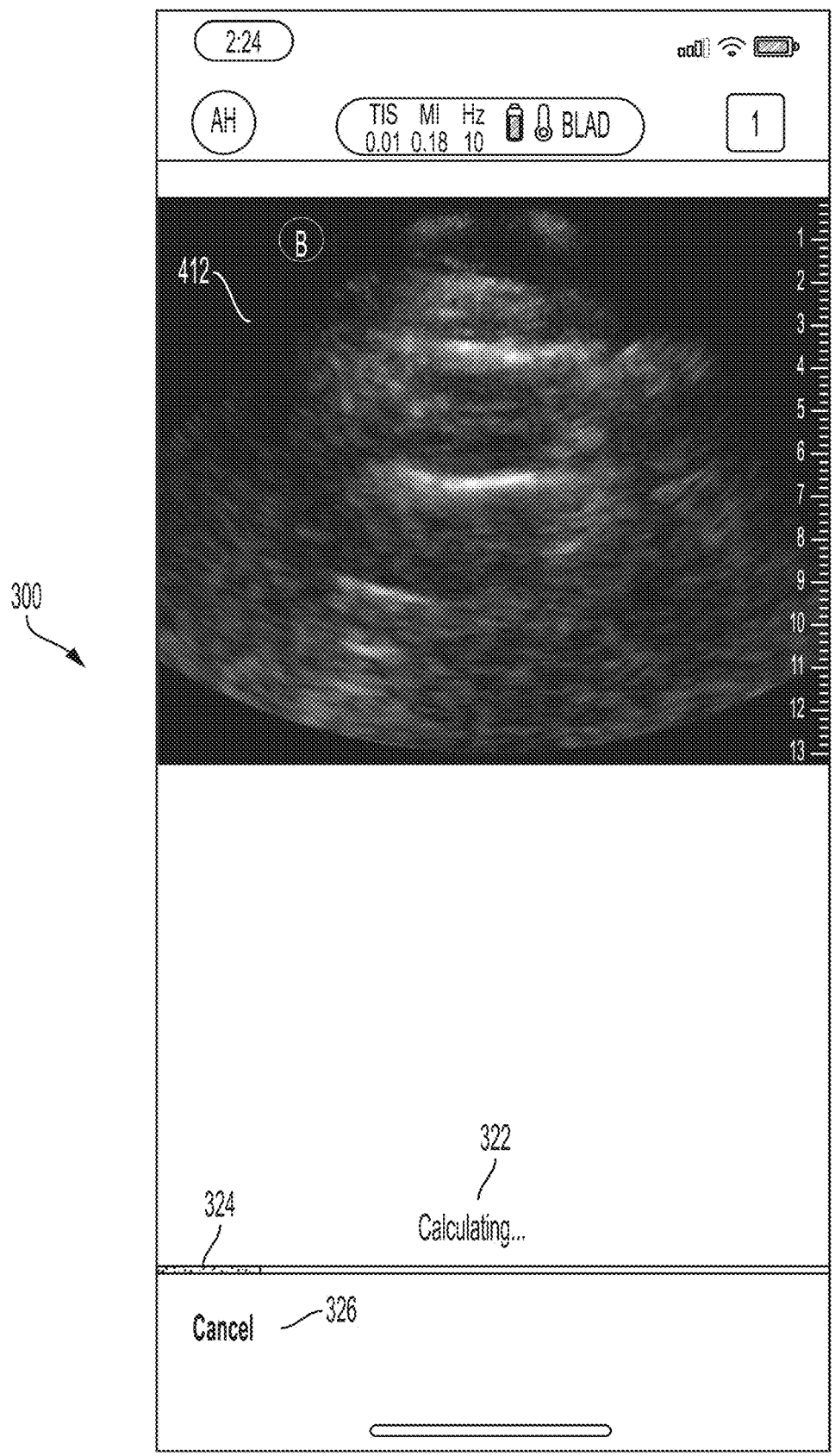
FIGS. 4, 5, 6, 7, 8, 9, 10, and 11 illustrate further examples of the GUI of FIG. 3.
Figure 5:
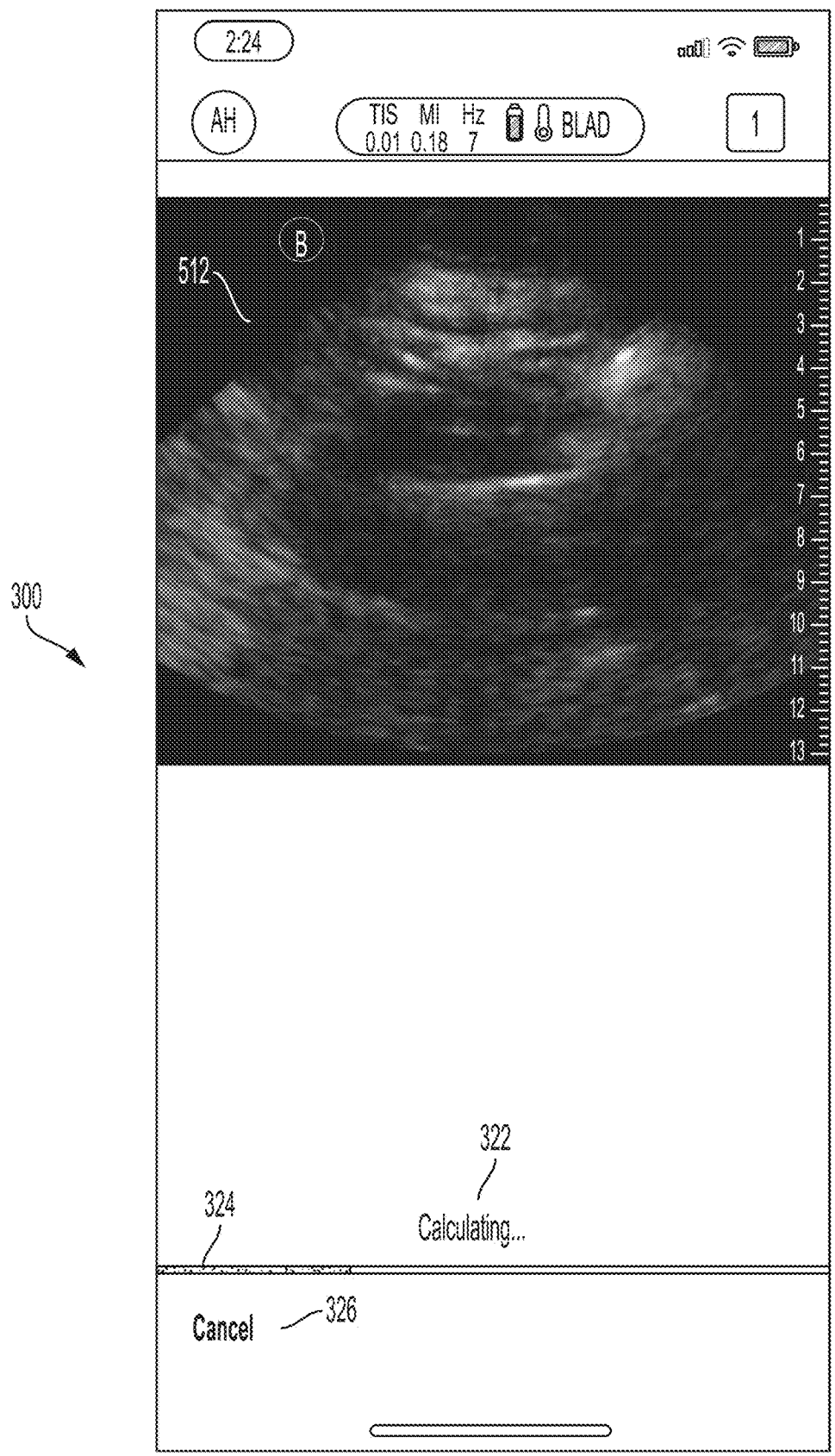
Figure 6:
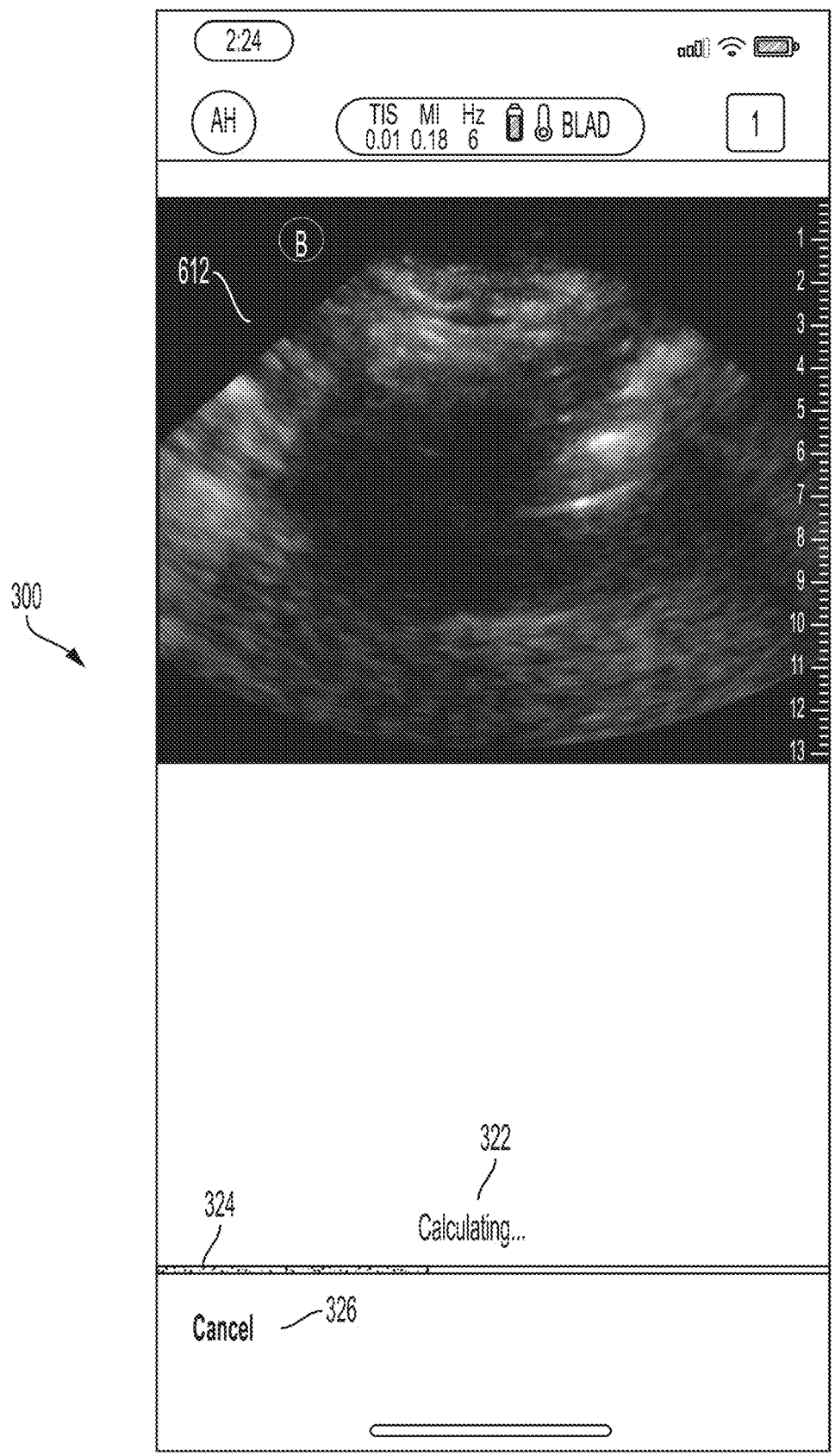
Figure 7:
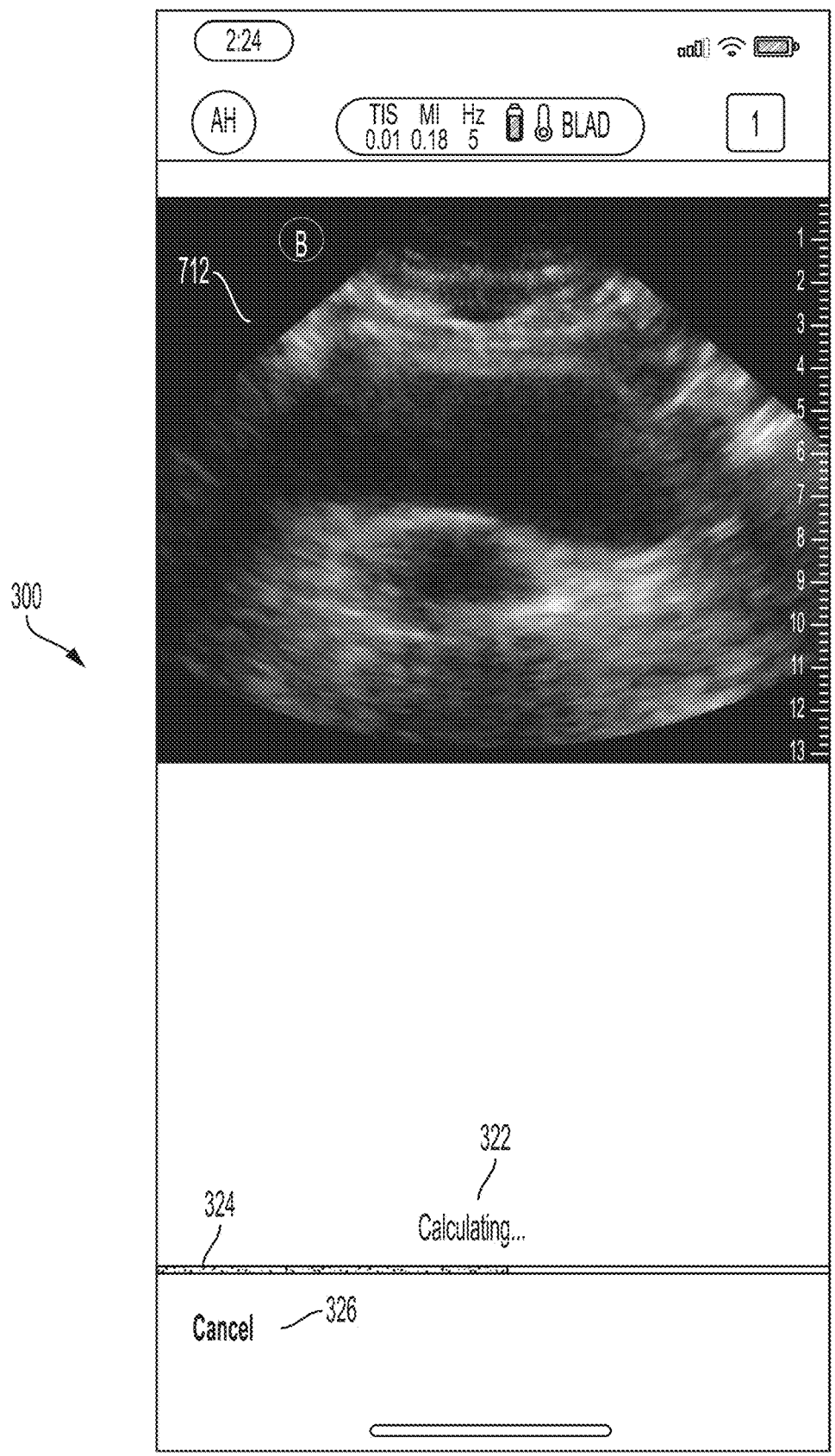
Figure 8:
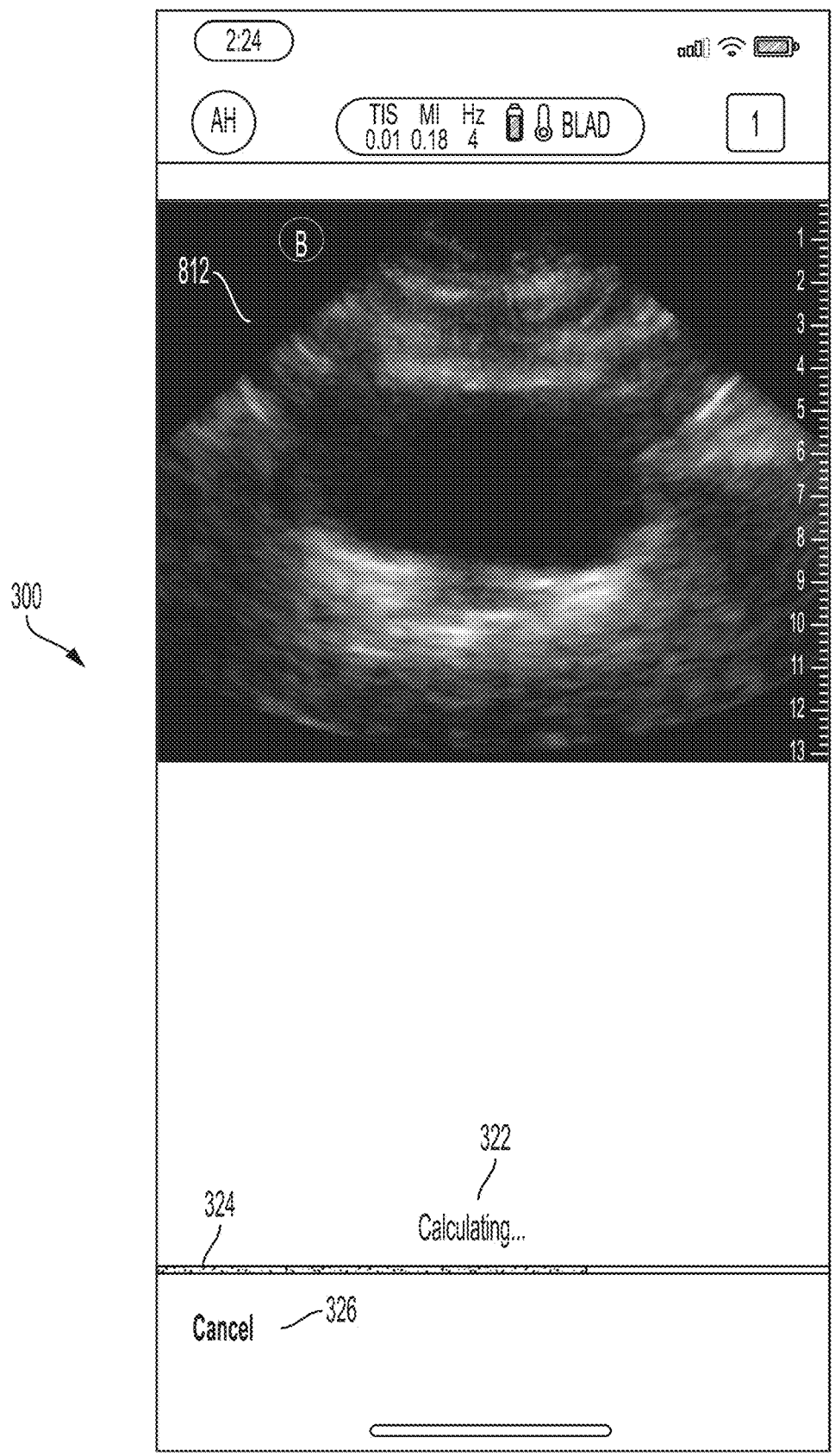
Figure 9:
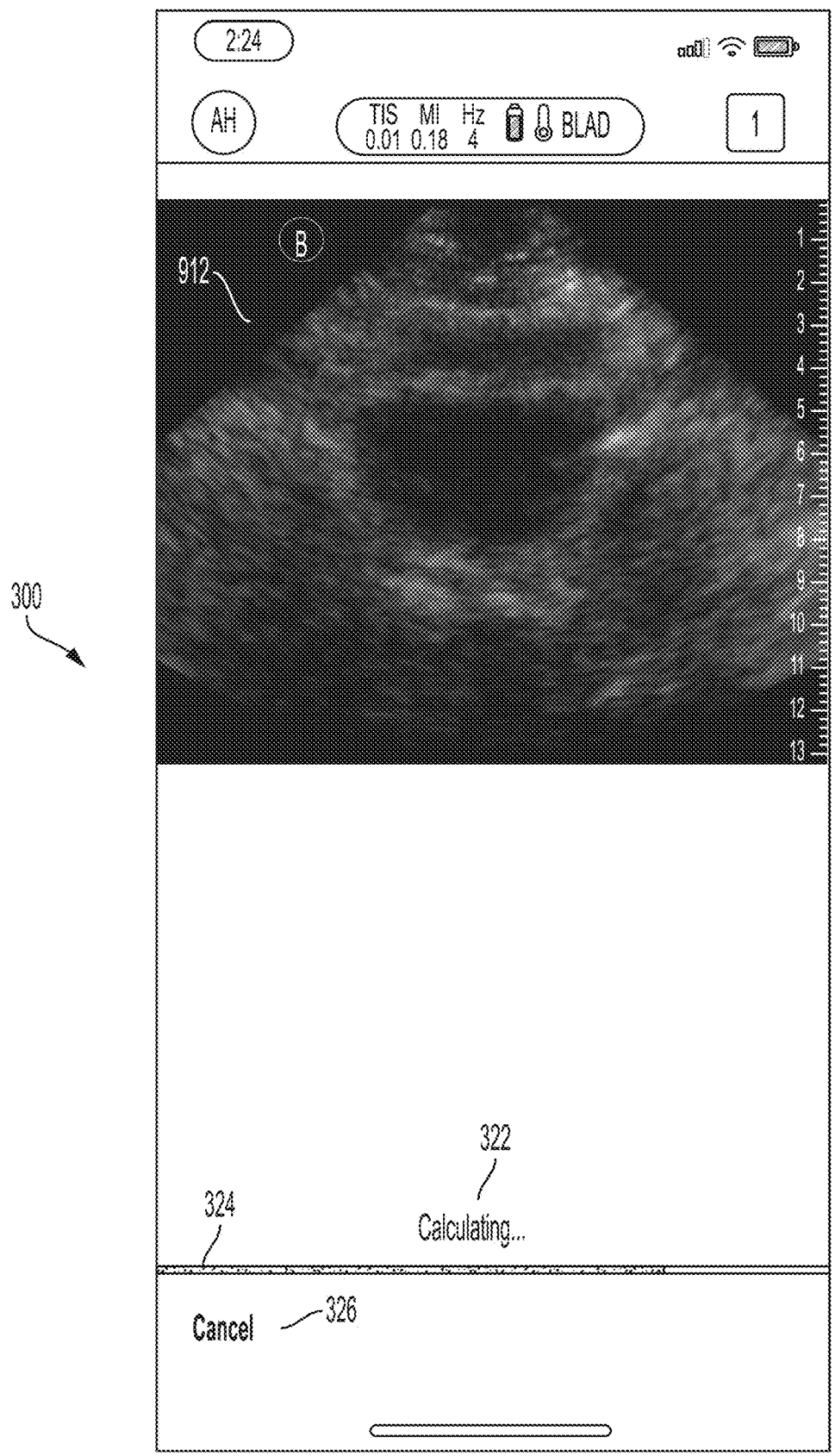
Figure 10:
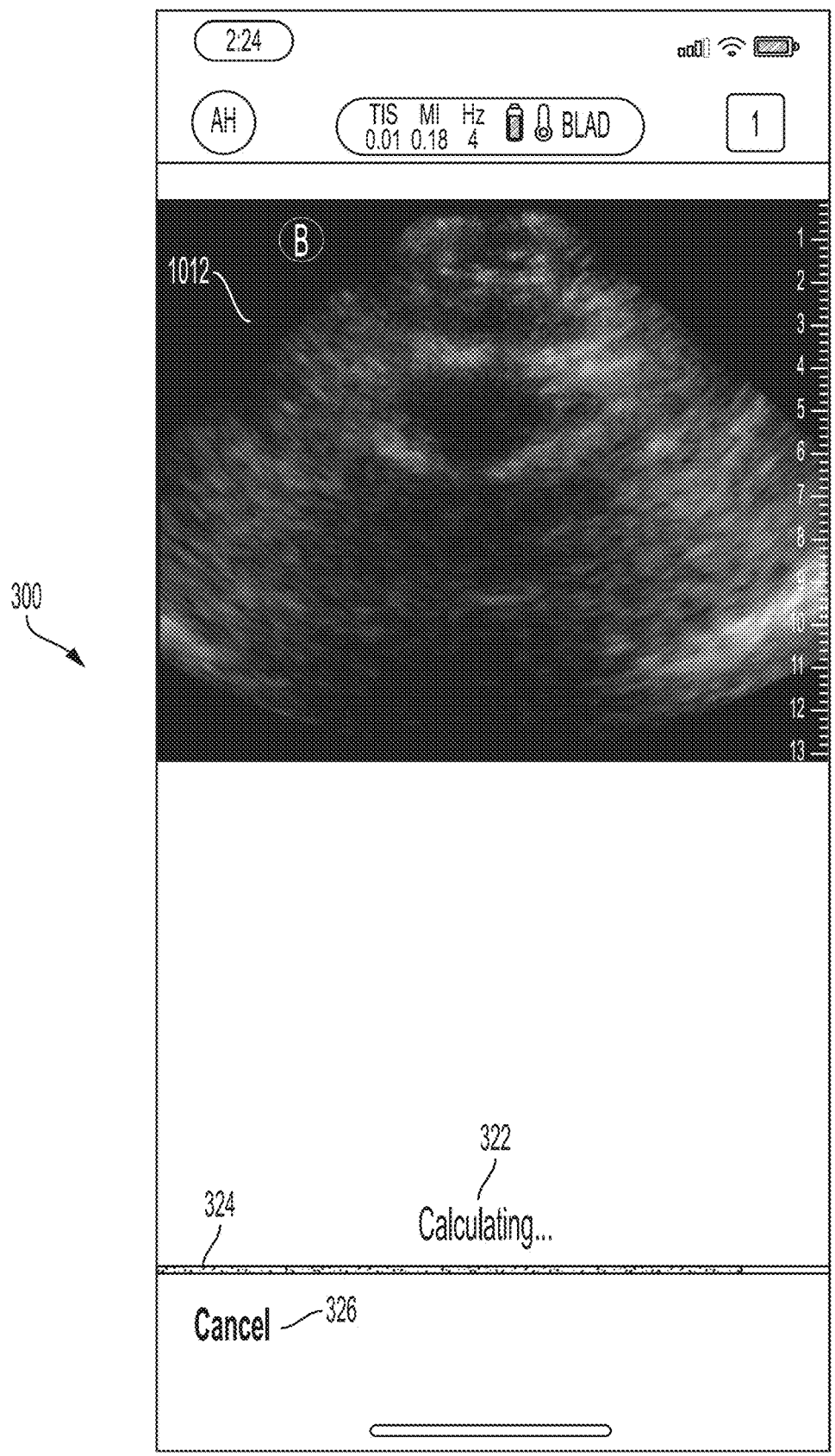
Figure 11:
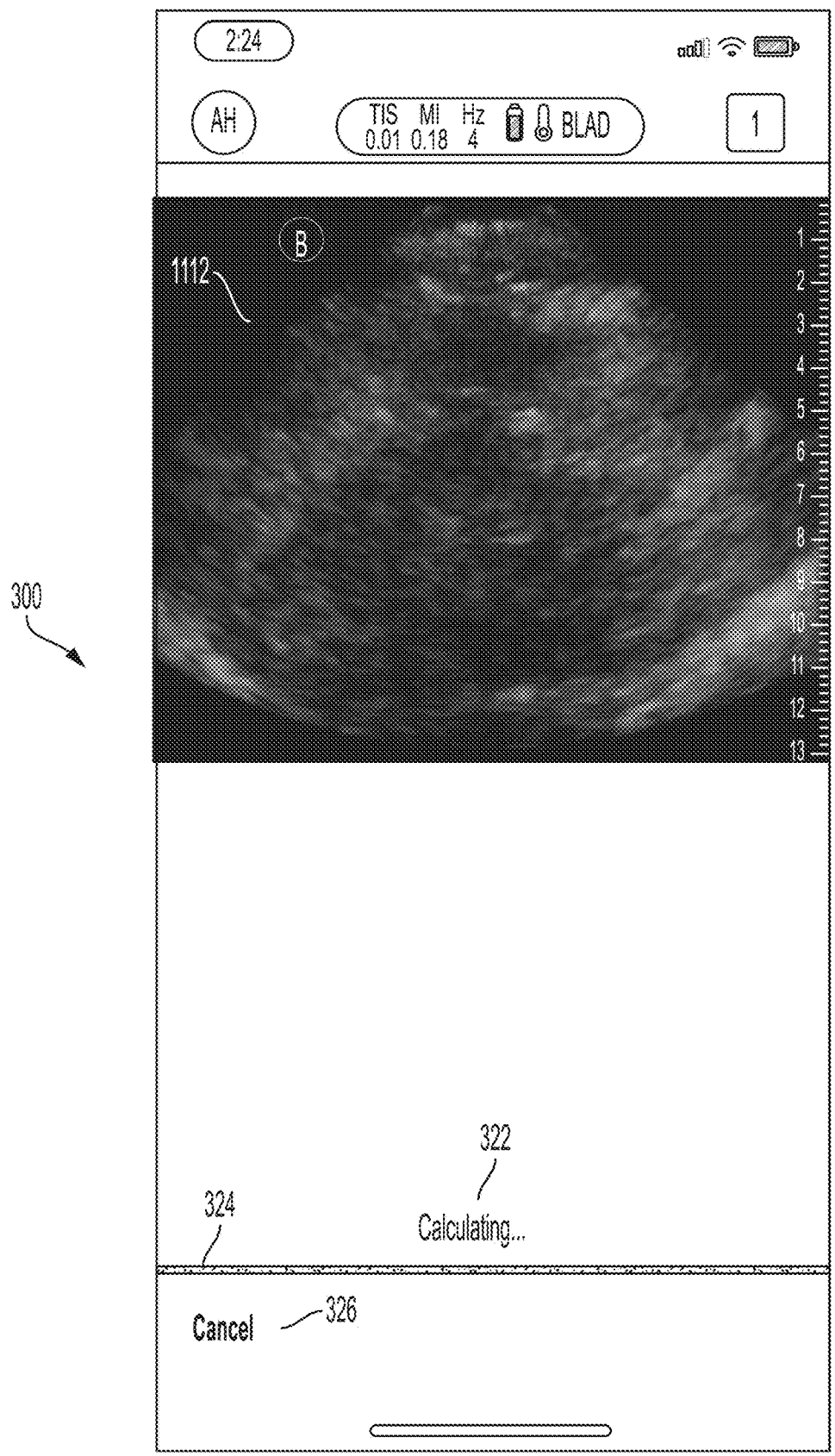

FIG. 4 illustrates another example of the GUI 300, in accordance with certain embodiments described herein. The GUI 300 in FIG. 4 includes an ultrasound image 412. The ultrasound image 412 may be the ultrasound image most recently collected during the 3D sweep, and the ultrasound image collected after the ultrasound image 312 was collected.

FIGS. 5-11 illustrate further examples of the GUI 300, in accordance with certain embodiments described herein. The GUI 300 in these figures includes an ultrasound image 512, 612, 712, 812, 912, 1012, or 1112, respectively. Each of the ultrasound images 512-1112 may be the ultrasound image collected most recently during the 3D sweep, and after the ultrasound image of the previous figure. It should be appreciated that the 3D sweep may collect more ultrasound images and the GUI 300 may therefore display more ultrasound images than illustrated in FIGS. 3-11. For example, the 3D sweep may collect 25 ultrasound images, each of which may be displayed by the GUI 300. In some embodiments, upon completing the 3D sweep, the processing device may display the GUI 1200 or the GUI 2100.

In some embodiments, the GUI 300 may further display a segmented portion that may be the interior of the bladder as depicted in the respective ultrasound image. Further description of segmented portions may be found with reference to the segmented portion 220. In such embodiments, the processing device may display the segmented portions on the respective ultrasound images in real-time as the ultrasound device collects the ultrasound images 312-1112.

Figure 12:
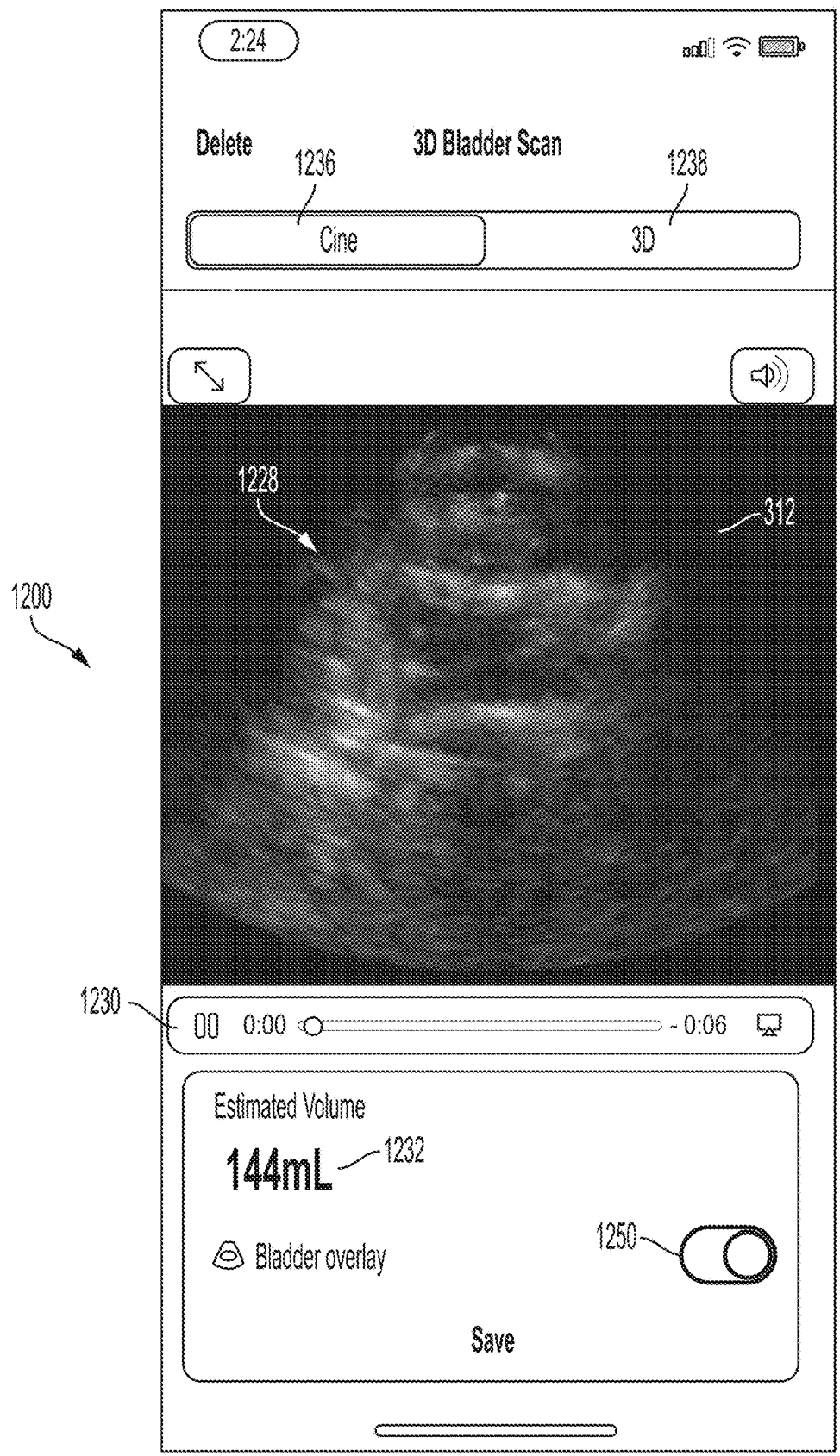
FIG. 12 illustrates another example GUI, in accordance with certain embodiments described herein.

FIG. 12 illustrates another example GUI 1200, in accordance with certain embodiments described herein. The GUI 1200 includes a cine 1228, a cine control/information bar 1230, a measurement value indicator 1232, a cine view indicator 1236, a 3D view indicator 1238, and a bladder overlay option 1250. The cine view indicator 1236 is highlighted in FIG. 12, indicating that the GUI 1200 is showing the 3D ultrasound data collected during the 3D sweep in the form of the cine 1228. In some embodiments, the cine 1228 may depict the ultrasound images that were collected during the 3D sweep (i.e., the ultrasound images 312-1112). In FIG. 12, the cine 1228 depicts the ultrasound image 312, namely the first ultrasound image collected during the 3D sweep. The cine control/information bar 1230 may control and provide information about the cine 1228. For example, the cine control/information bar 1230 may provide information about how much time has elapsed during playback of the cine 1228, how much time remains for playback of the cine 1228, and may control playing, pausing, or changing to a different point in the cine 1228. In some embodiments, the cine 1228 may play in a loop. As described further below, the GUI 1200 may display segmented portions with certain ultrasound images. The bladder overlay option 1250 may toggle display of such segmented portions on or off.

In some embodiments, the measurement value indicator 1232 may display a value for a measurement performed on the ultrasound images collected during the sweep. For example, the measurement may be a measurement of the volume of the bladder depicted in the ultrasound images collected during the sweep. In some embodiments, to perform a volume measurement, the processing device may calculate the area of the segmented portions (if any) in each ultrasound image. The processing device may then calculate the average area of the segmented portions in each successive pair of ultrasound images in the 3D sweep (e.g., the average of the segmented portions in the first and second ultrasound images, the average of the segmented portions in second and third ultrasound images, etc.). The processing device may then multiply each averaged area by the angle (in radians) between each successive imaging slice in the 3D sweep to produce a volume, and sum all the volumes to produce the final volume value. It should be appreciated that other methods for performing measurements based on ultrasound images may be used, and other types of measurements may also be performed.

As described above, in some embodiments the processing device may display the GUI 1200 upon completing the 3D sweep. Upon receiving selection of the 3D view indicator 1238 from the GUI 1200, the processing device may display the GUI 2100.

Figure 13:
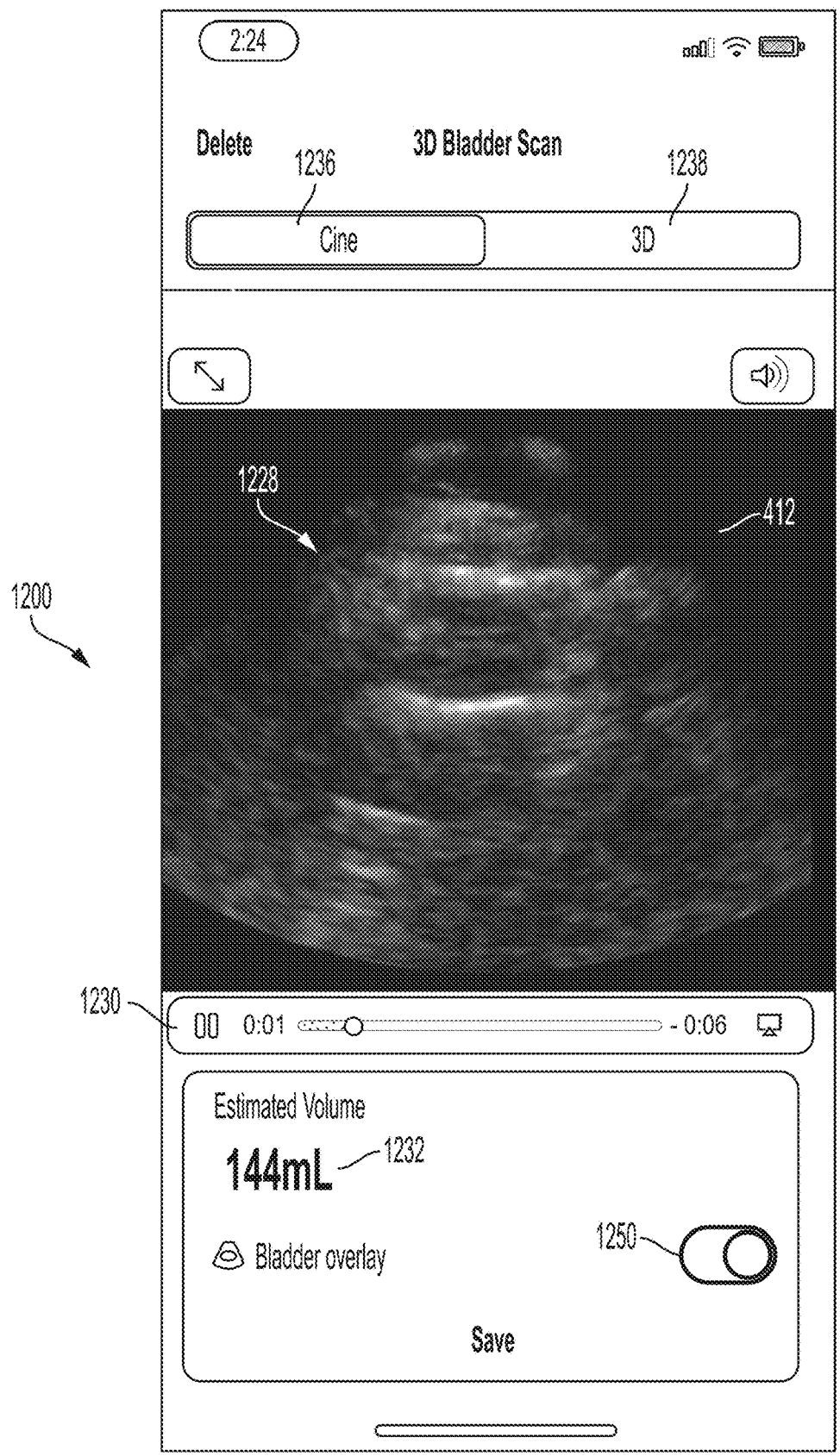
FIGS. 13, 14, 15, 16, 17, 18, 19, and 20 illustrate further examples of the GUI of FIG. 12, in accordance with certain embodiments described herein.
Figure 14:
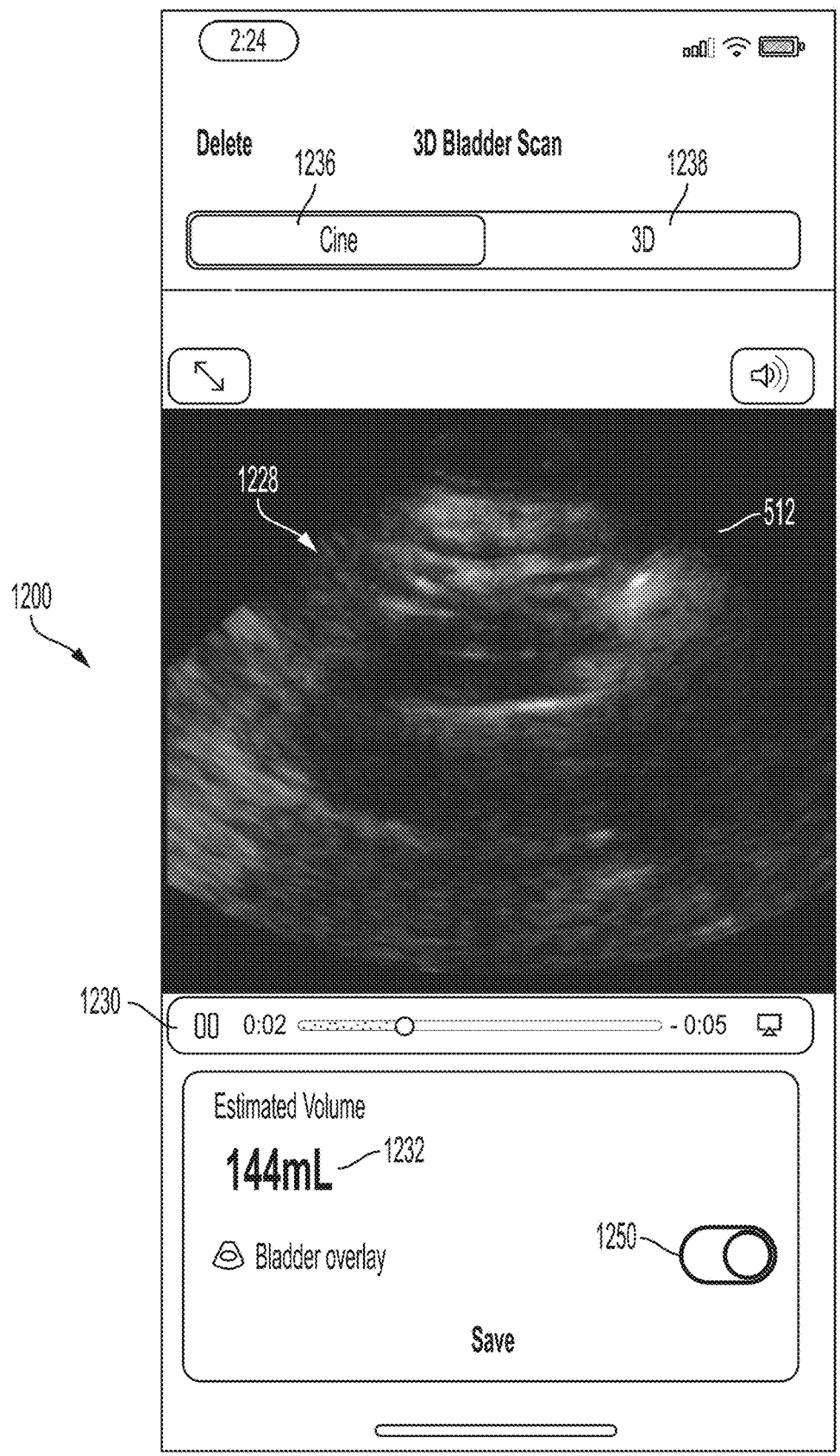
Figure 15:
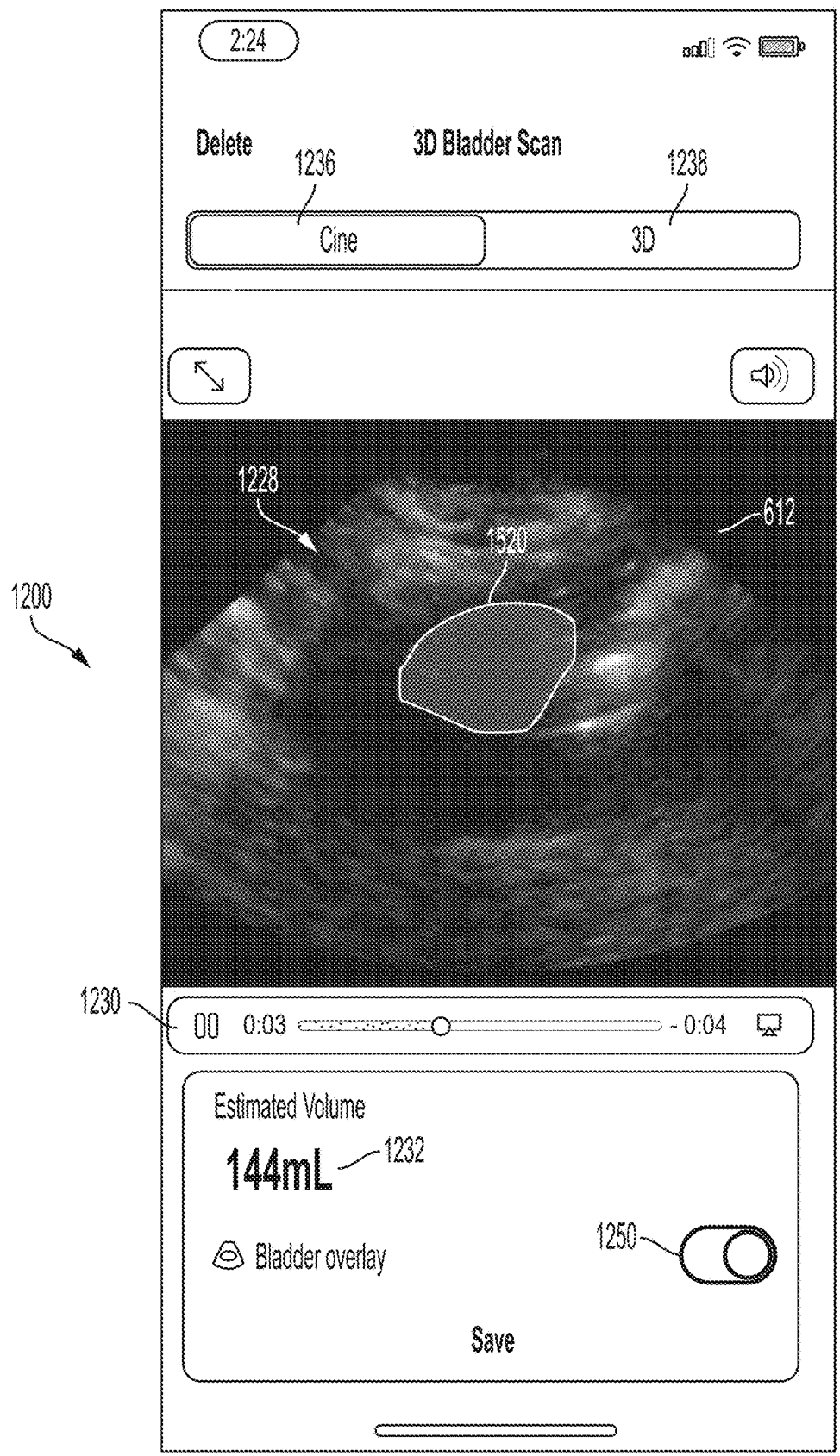

FIG. 13 illustrates another example of the GUI 1200, in accordance with certain embodiments described herein. In FIG. 13, the cine 1228 depicts the ultrasound image 412, namely the ultrasound image collected during the 3D sweep after the ultrasound image 312 that was displayed in FIG. 12.

Figure 16:
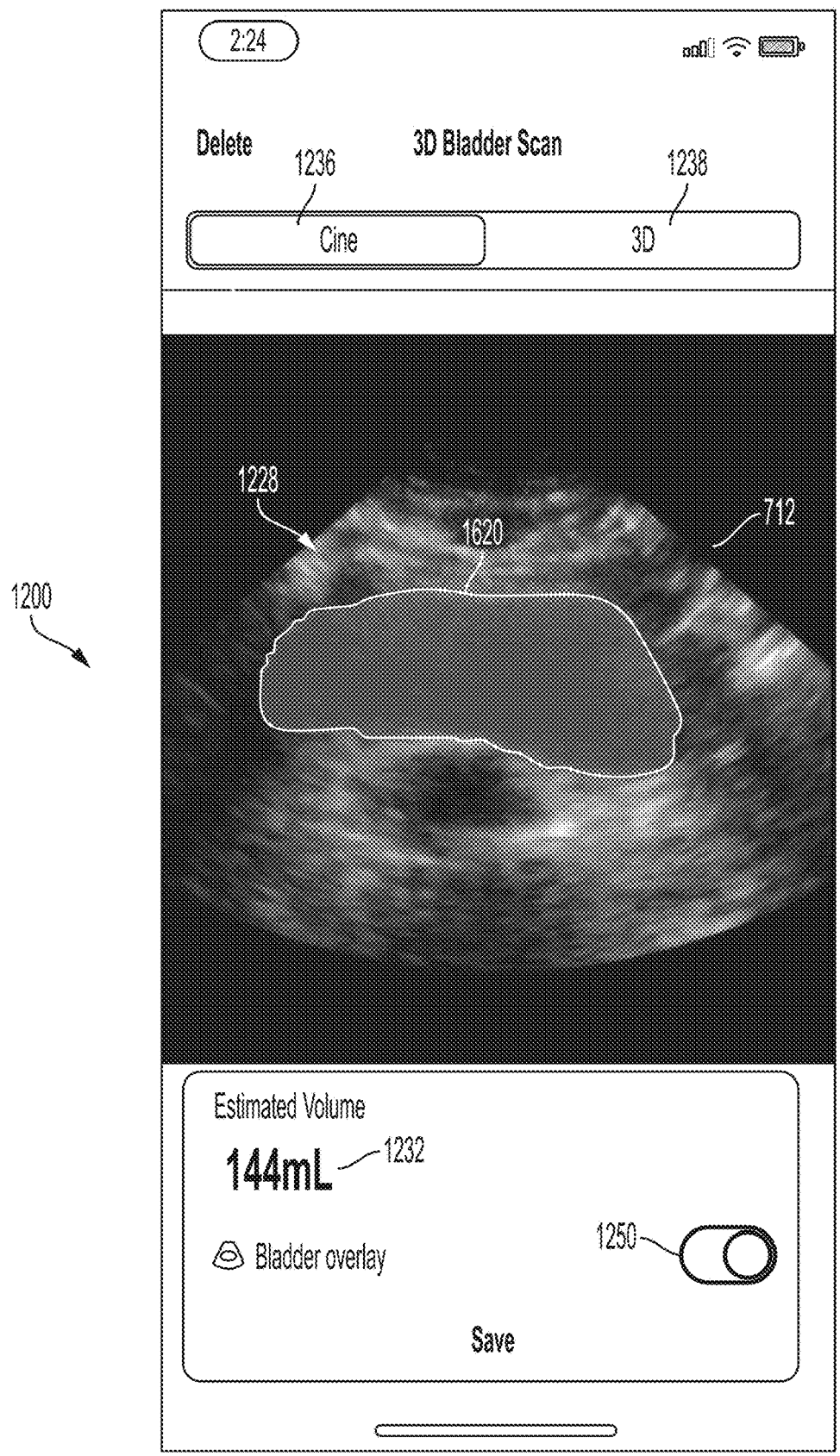
Figure 17:
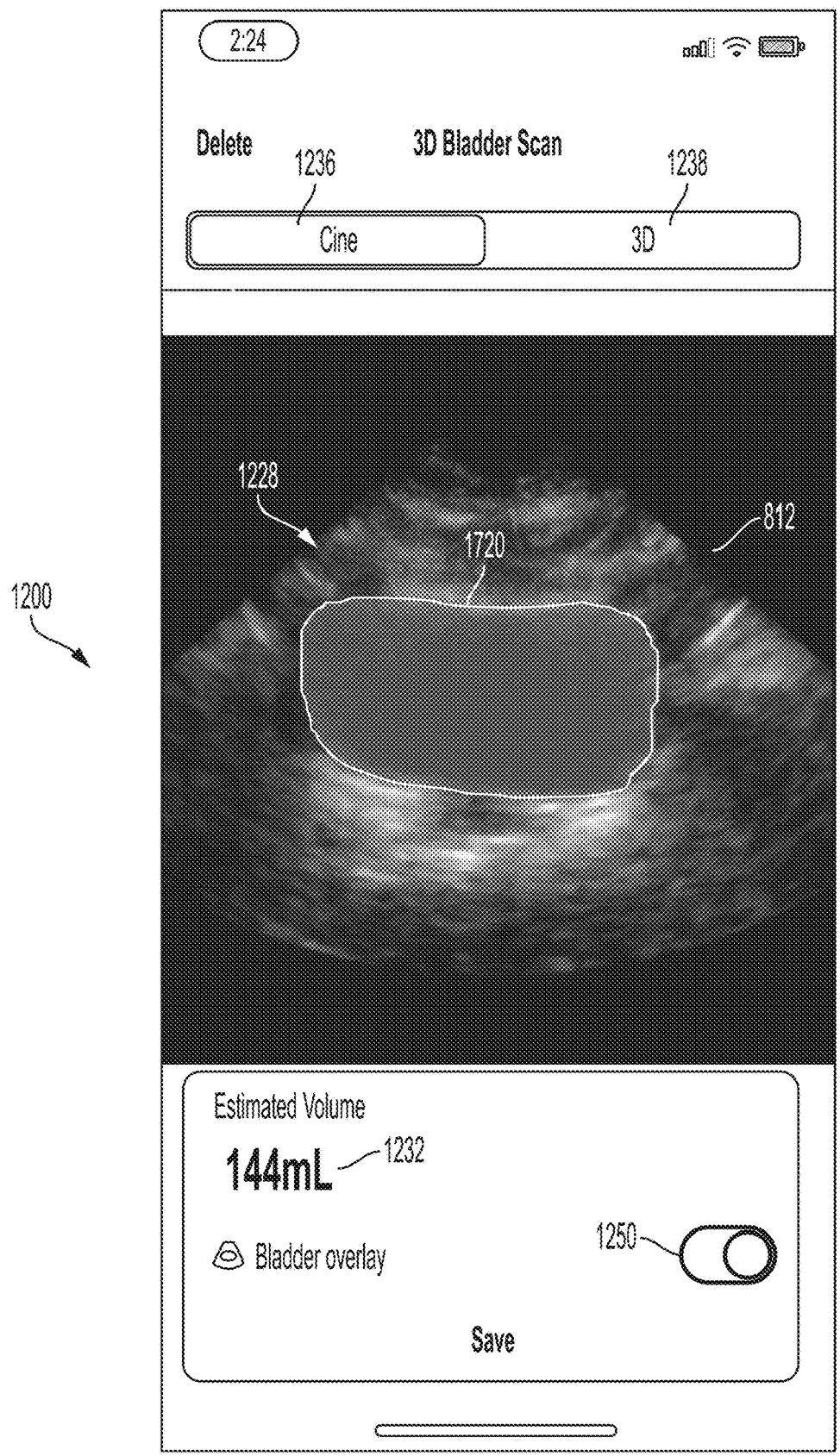
Figure 18:
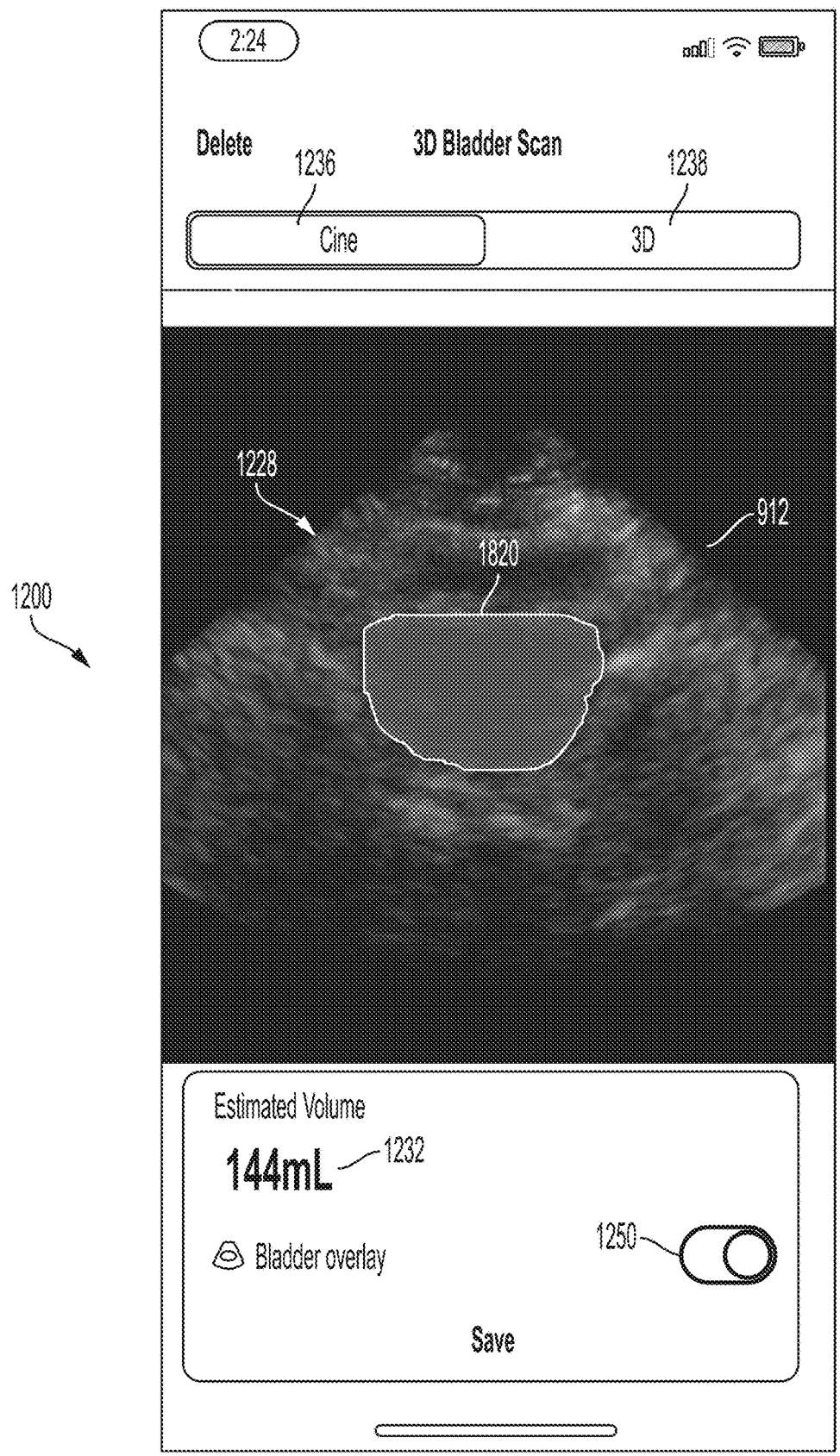
Figure 19:
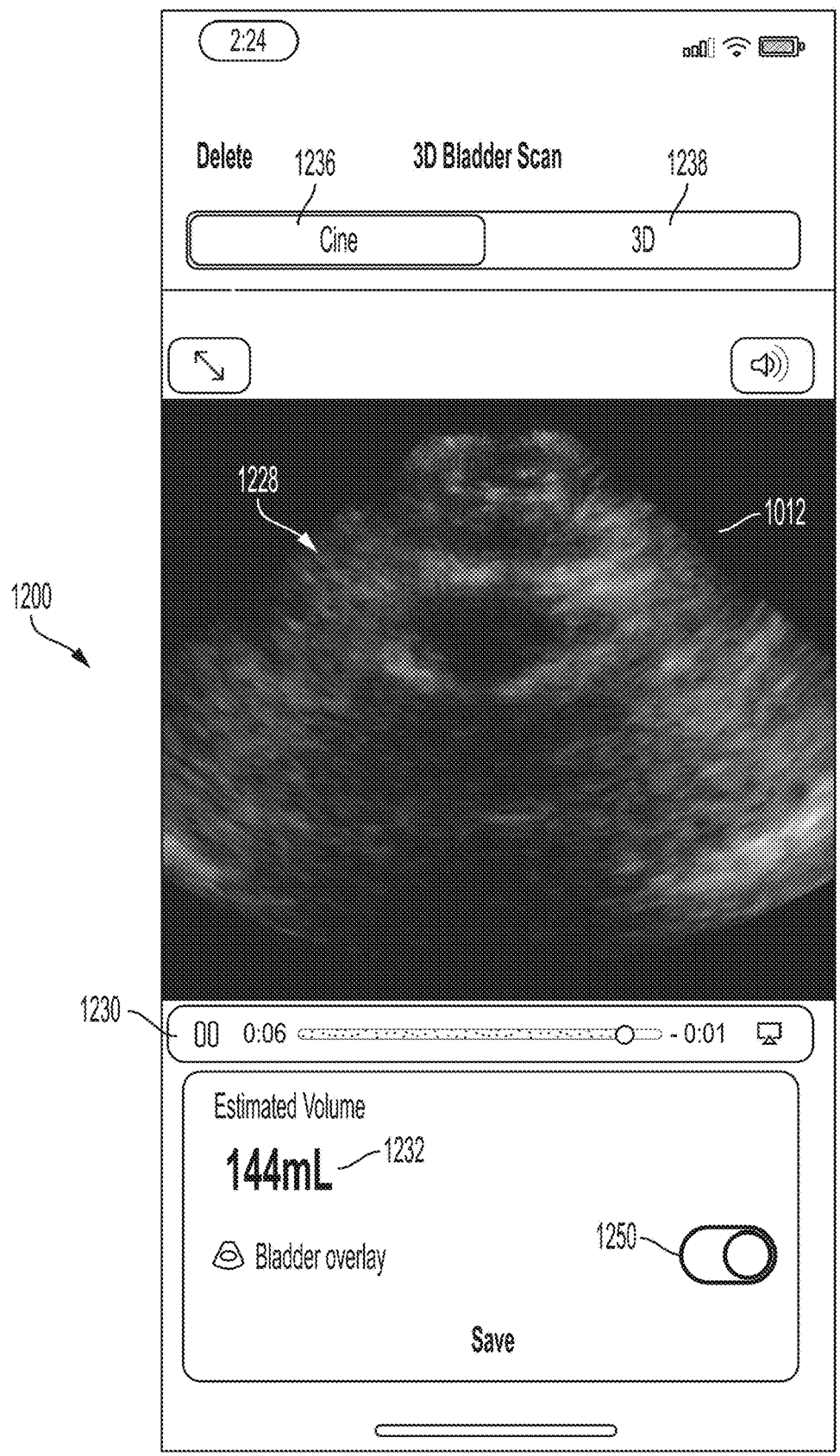
Figure 20:
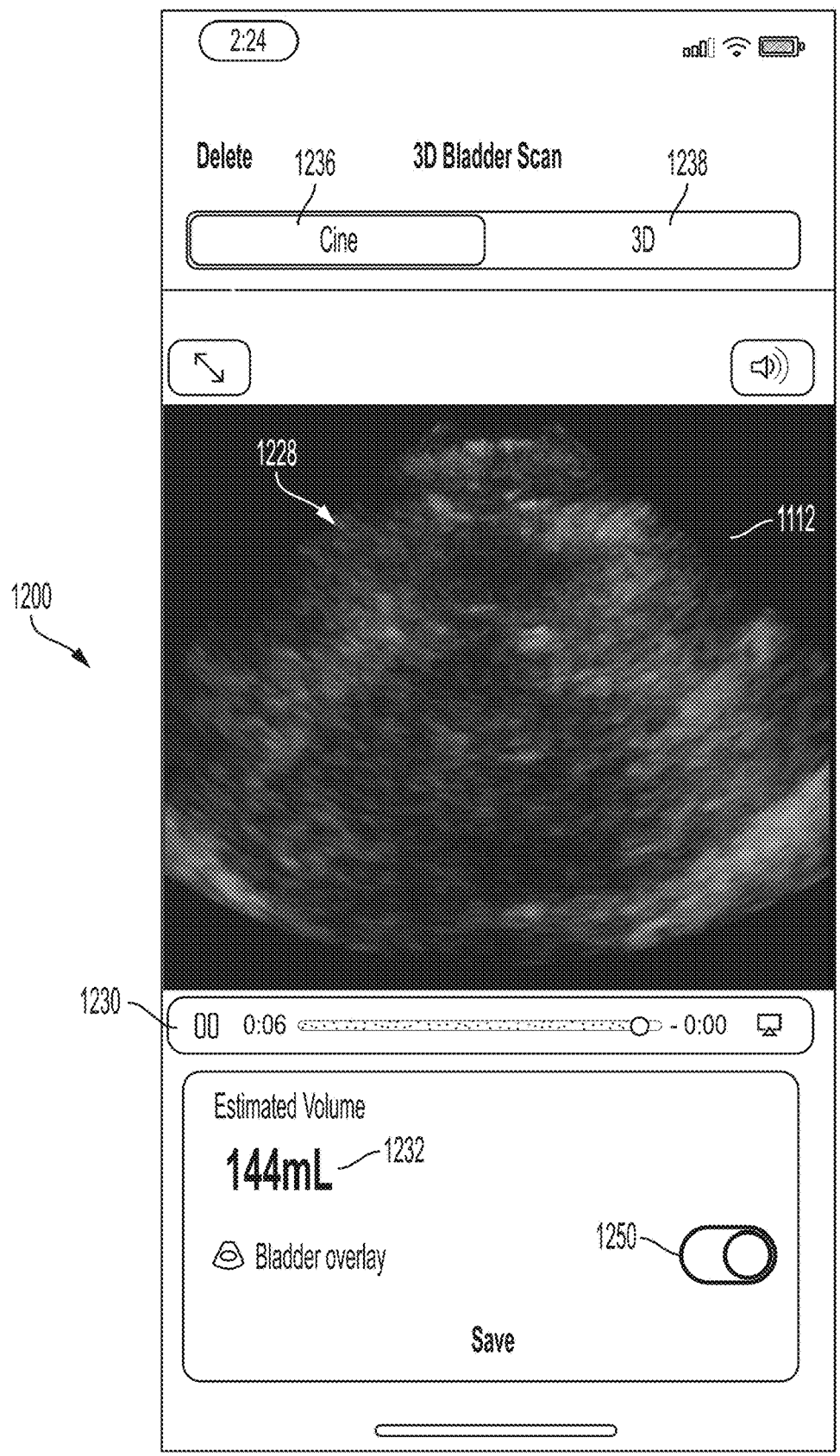

FIGS. 14-20 illustrate further examples of the GUI 1200, in accordance with certain embodiments described herein. In each figure, the cine 1228 depicts the ultrasound image 512, 612, 712, 812, 912, 1012, or 1112, respectively. Each of the ultrasound images 512-1112 is one of the ultrasound images collected during the 3D sweep and after the ultrasound image depicted in the previous figure. FIGS. 15-18 further include a segmented portion 1520, 1620, 1720, or 1820, respectively. Each of the segmented portions 1520-1820 may be the interior of the bladder as depicted in the respective ultrasound image 612, 712, 812, and 912. Further description of segmented portions may be found with reference to the segmented portion 220. As described above, the bladder overlay option 1250 may toggle display of these segmented portions on or off. It should be appreciated that in FIGS. 12-14 and 19-20, the bladder is not depicted in the respective ultrasound images 312-512 and 1012-1112, and thus no segmented portion is displayed. It should also be appreciated that, as depicted in FIGS. 16-18, in some embodiments the cine control/information bar 1230 may cease to be displayed if the processing device does not receive a selection of one of its features during a threshold period of time. As described above, it should be appreciated that the 3D sweep may collect more ultrasound images and the GUI 1200 may therefore display more ultrasound images and segmented portions than illustrated in FIGS. 3-11. For example, the 3D sweep may collect 25 ultrasound images, each of which may be displayed by the GUI 300.

Figure 21:
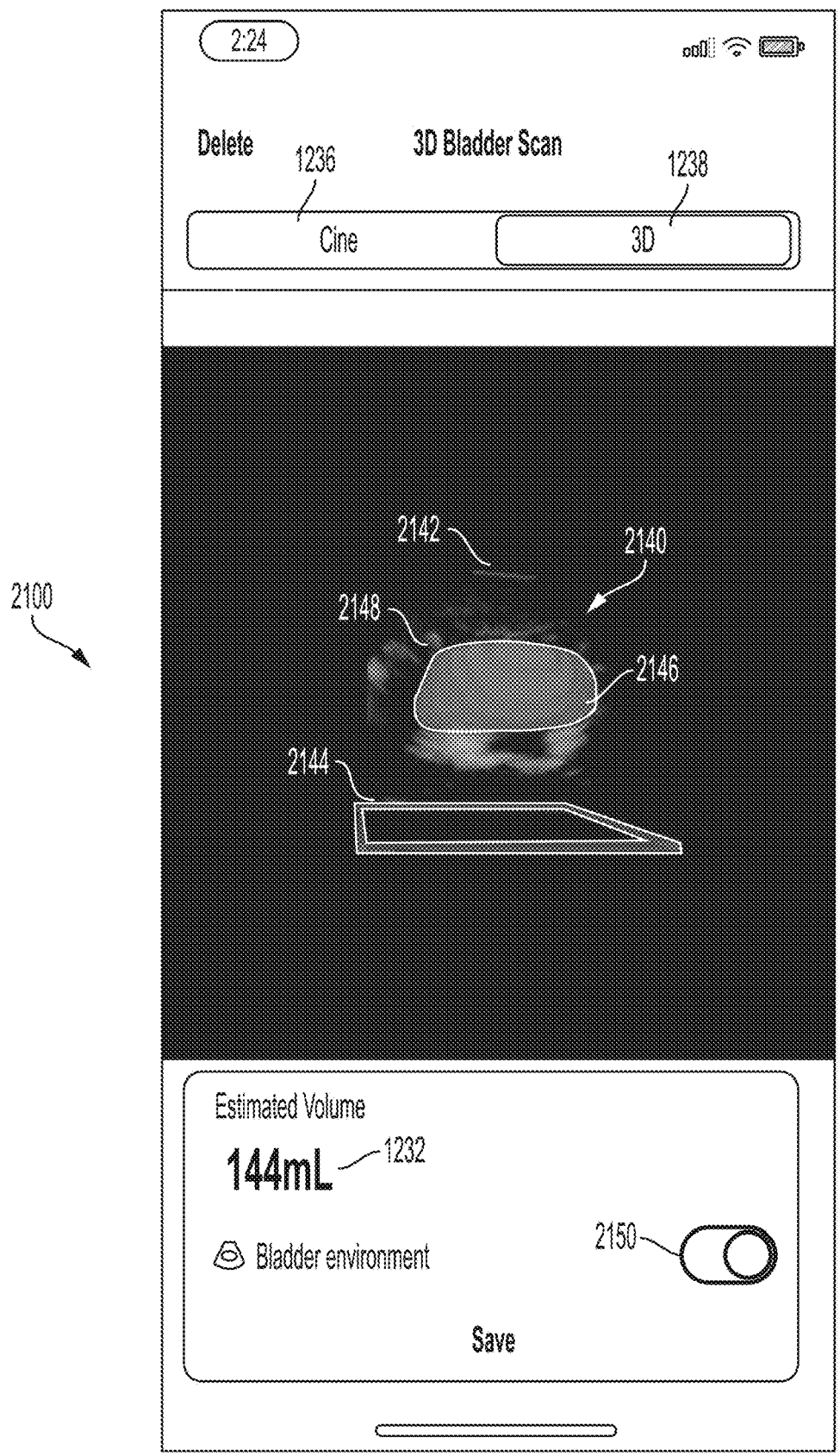
FIG. 21 illustrates another example GUI, in accordance with certain embodiments described herein.

FIG. 21 illustrates another example GUI 2100, in accordance with certain embodiments described herein. The GUI 2100 includes the cine view indicator 1236, the 3D view indicator 1238, the measurement value indicator 1232, a 3D visualization 2140, a first orientation indicator 2142, and a second orientation indicator 2144. The 3D visualization 2140 includes a 3D bladder visualization 2146 and a 3D environment visualization 2148.

In some embodiments, the 3D visualization 2140 may be generated from the ultrasound images collected during the 3D sweep and segmented portions from the ultrasound images. Each ultrasound image may be generated from an imaging slice arranged at a different angle relative to the ultrasound device. The processing device may arrange data from both the segmented portions of the ultrasound images (which may be generated by a statistical model, as described above) and the B-mode ultrasound images themselves at the corresponding angle of the ultrasound image relative to the ultrasound device, and convert these angled images into a grid of voxels. The processing device may then produce the 3D visualization 2140 by volume rendering the grid of voxels. More particularly, in some embodiments, the 3D visualization 2140 may be a combination (e.g., a linear combination) of data from the segmented portions of the ultrasound images and the ultrasound images themselves. For example, the RGBA value at a given voxel depicted by the 3D visualization 2140 may be based on f(BladderIntensity)+g(TissueIntensity). BladderIntensity may be the value of a segmentation mask at that voxel, where the segmentation mask is used to generate a segmented portion as described above. TissueIntensity may be the value of a B-mode ultrasound image at that voxel. f(x) may take endpoints rmax and rmin of ranges for each of red, green, blue, and alpha in the RGBA space and return an interpolated value (x−rmin)/(rmax−rmin) for each of red, green, blue, and alpha. g(x) may be a scaling factor multiplied by x. Multiple ultrasound images and segmentation masks may overlap at a given voxel when generating the 3D visualization 2140, and the f(BladderIntensity)+g(TissueIntensity) value for each may be added to produce the final value for a voxel. When displayed, the 3D visualization 2140 generated as described above may include a 3D bladder visualization 2146 portion that may depict the 3D volume of the bladder and as well as a 3D environment visualization 2148 portion that may depict surrounding tissue. The 3D environment visualization 2148 may highlight the boundary of the bladder and provide orientation in three-dimensional space of the bladder by depicting surrounding landmarks (e.g., the pubic bone) using the ultrasound image component of the 3D visualization 2140. The bladder environment option 2150 may toggle display of the 3D environment visualization 2148 on or off. Thus, if the bladder environment option 2150 is set on, the 3D bladder visualization 2146 and the 3D environment visualization 2148 may be displayed, and if the bladder environment option 2150 is set off, the 3D bladder visualization 2146 but not the 3D environment visualization 2148 may be displayed.

In some embodiments, the first orientation indicator 2142 may be an indicator of the position of the ultrasound device that performed the 3D sweep relative to the bladder depicted by the 3D visualization 2140. In some embodiments, the second orientation indicator 2144 may be an indicator of the position of the bottom plane of the ultrasound images collected during the 3D sweep relative to the bladder depicted by the 3D visualization 2140. Thus, the positions of the first orientation indicator 2142 and/or the second orientation indicator 2144 relative to the 3D visualization 2140 in the GUI 2100 may provide information about the orientation of the 3D visualization 2140 as depicted in the GUI 2100.

Figure 22:
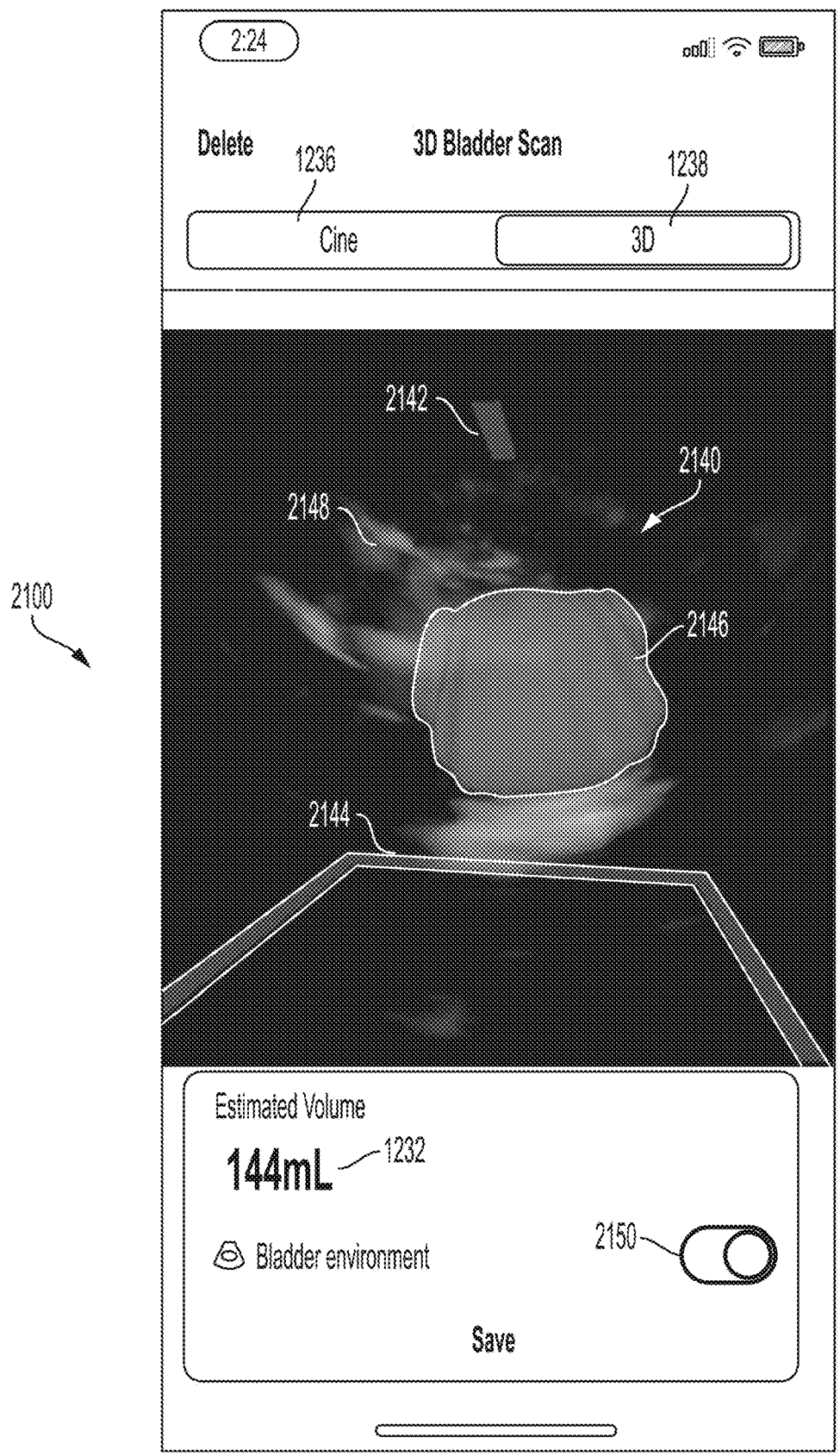
FIG. 22 illustrates a further example of the GUI of FIG. 21, in accordance with certain embodiments described herein.

In some embodiments, the processing device may detect a dragging or pinching movement across its touch-sensitive display screen and, based on the dragging or pinching movement, modify the display of the 3D visualization 2140, the first orientation indicator 2142, and the second orientation indicator 2144 to depict them as if they were being rotated and/or zoomed in three dimensions. For example, in response to a horizontal dragging movement across a touch-sensitive display screen of the processing device, the processing device may display the 3D visualization 2140, the first orientation indicator 2142, and the second orientation indicator 2144 such that they appear to be rotated in three dimensions about a vertical axis. In response to a vertical dragging movement, the processing device may display the 3D visualization 2140, the first orientation indicator 2142, and the second orientation indicator 2144 such that they appear to be rotated in three dimensions about a horizontal axis. In response to a pinching movement, the processing device may display the 3D visualization 2140, the first orientation indicator 2142, and the second orientation indicator 2144 such that they appear zoomed in. FIG. 22 illustrates a further example of the GUI 2100, in accordance with certain embodiments described herein. In FIG. 22, the 3D visualization 2140, the first orientation indicator 2142, and the second orientation indicator 2144 are displayed after the processing device receives a dragging movement and a pinching movement across a touch-sensitive display screen of the processing device. The processing device displays the 3D visualization 2140, the first orientation indicator 2142, and the second orientation indicator 2144 to appear as if they have been rotated in three dimensions and zoomed in.

As described above, in some embodiments the processing device may display the GUI 2100 upon completing the 3D sweep. Upon receiving selection of the cine view indicator 1236 from the GUI 2100, the processing device may display the GUI 1200.

Figure 23:
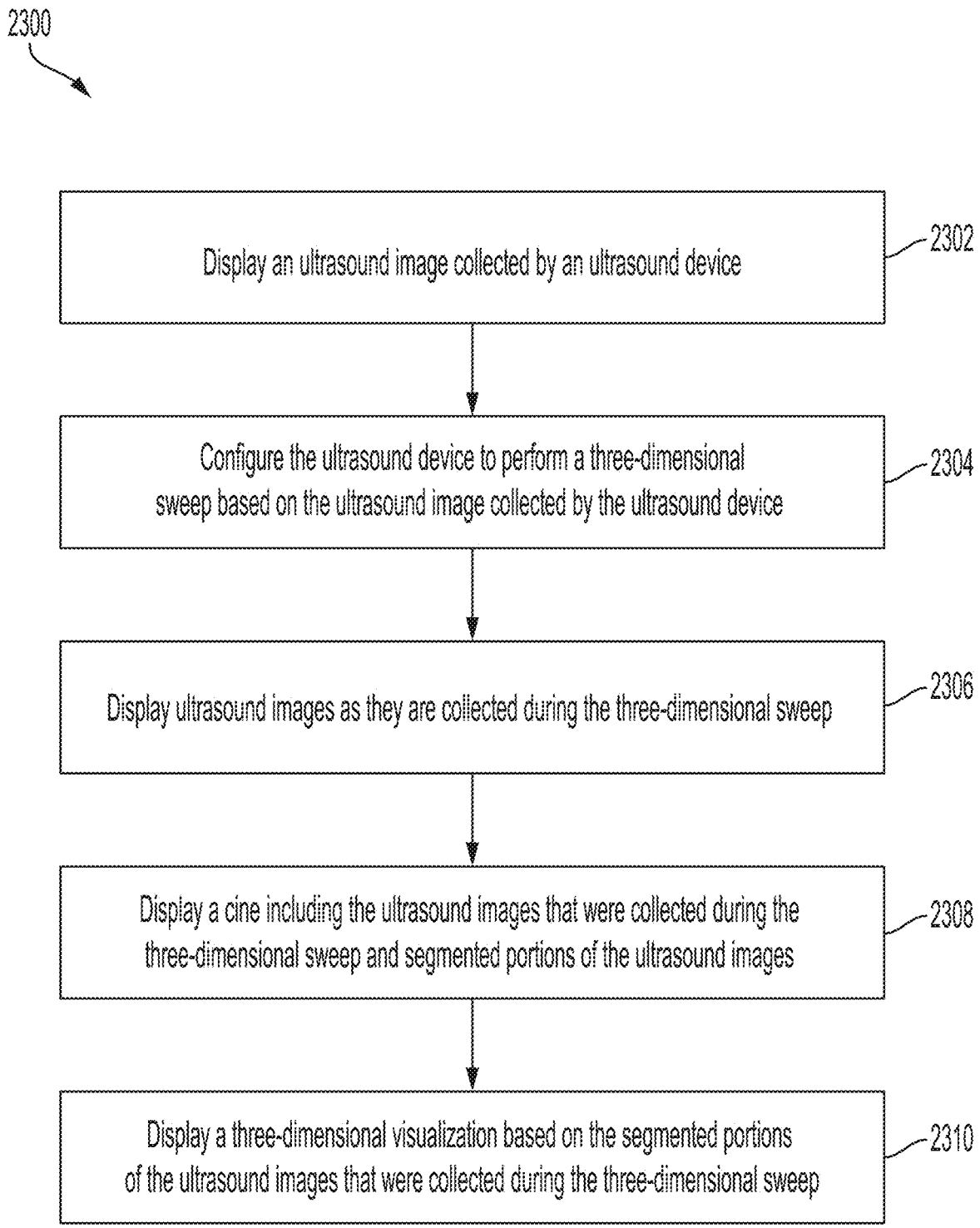
FIG. 23 illustrates a process for collection of visualization of ultrasound data, in accordance with certain embodiments described herein.

FIG. 23 illustrates a process 2300 for collection of visualization of ultrasound data, in accordance with certain embodiments described herein. The process 2300 is performed by a processing device. The processing device may be, for example, a handheld device such as a mobile phone or tablet, or a laptop, and may be in operative communication with an ultrasound device. The ultrasound device and the processing device may communicate over a wired communication link (e.g., over Ethernet, a Universal Serial Bus (USB) cable or a Lightning cable) or over a wireless communication link (e.g., over a BLUETOOTH, WiFi, or ZIGBEE wireless communication link). The processing device may have a touch-sensitive display screen.

In act 2302, the processing device displays an ultrasound image collected by an ultrasound device. In some embodiments, the processing device may also display a segmented portion of the ultrasound image. Further description of act 2302 may be found with reference to FIG. 2. The process 2300 proceeds from act 2302 to act 2304.

In act 2304, the processing device configures the ultrasound device to perform a 3D sweep based on the ultrasound image from act 2302 that was collected by the ultrasound device. Further description of act 2304 may be found with reference to FIG. 2. The process 2300 proceeds from act 2304 to act 2306.

In act 2306, the processing device displays ultrasound images as they are collected during the 3D sweep. In some embodiments, the processing device may also display segmented portions of the ultrasound images as they are collected during the 3D sweep. Further description of act 2306 may be found with reference to FIGS. 3-11. The process 2300 proceeds from act 2306 to act 2308.

In act 2308, the processing device displays a cine including the ultrasound images and segmented portions of the ultrasound images that were collected during the 3D sweep. Further description of act 2308 may be found with reference to FIGS. 12-20. The process 2300 proceeds from act 2308 to act 2310.

In act 2310, the processing device displays a three-dimensional visualization based on the segmented portions of the ultrasound images collected during the 3D sweep. Further description of act 2310 may be found with reference to FIGS. 21-22.

In some embodiments, act 2302 may be absent. For example, the processing device may receive a selection from the GUI 100 to initiate the 3D sweep, and may not display the GUI 200. In some embodiments, act 2306 may be absent. For example, the processing device may not display the GUI 1200 during the 3D sweep. In some embodiments, act 2308 may be absent. For example, the processing device may display the GUI 2100 after the GUI 300 and not display the GUI 1200. In some embodiments, act 2310 may be absent. For example, the processing device may display the GUI 1200 after the GUI 300 and not display the GUI 2100. In some embodiments, act 2310 may precede act 2308. For example, the processing device may display the GUI 2100 before the GUI 1200.

Various inventive concepts may be embodied as one or more processes, of which an example has been provided. The acts performed as part of each process may be ordered in any suitable way. Thus, embodiments may be constructed in which acts are performed in an order different than illustrated, which may include performing some acts simultaneously, even though shown as sequential acts in illustrative embodiments. Further, one or more of the processes may be combined and/or omitted, and one or more of the processes may include additional steps.

While the above description has focused on imaging, measurement and visualization of a bladder, it should be appreciated that other anatomical structures (e.g., the left ventricle of the heart) may be imaged, measured, and visualized in the same manner.

The above description has focused on displaying ultrasound images, segmented portions, and three-dimensional visualization based on such segmented portions, where the ultrasound images were collected during a 3D sweep. As described above, in some embodiments, the processing device may configure the ultrasound device and/or itself to use beamforming to focus an ultrasound beam along a different direction at each stage of the 3D sweep. However, it should be appreciated that the same methods may be used to display ultrasound images, segmented portions, and three-dimensional visualization based on such segmented portions, where the ultrasound images were collected from a single ultrasound beam that collects three-dimensional data. Alternatively, the same methods may be used for ultrasound images that were collected when the ultrasound device focuses an ultrasound along one direction, and a user moves the ultrasound device to sweep this beam in order to collect three-dimensional data.

Figure 24:
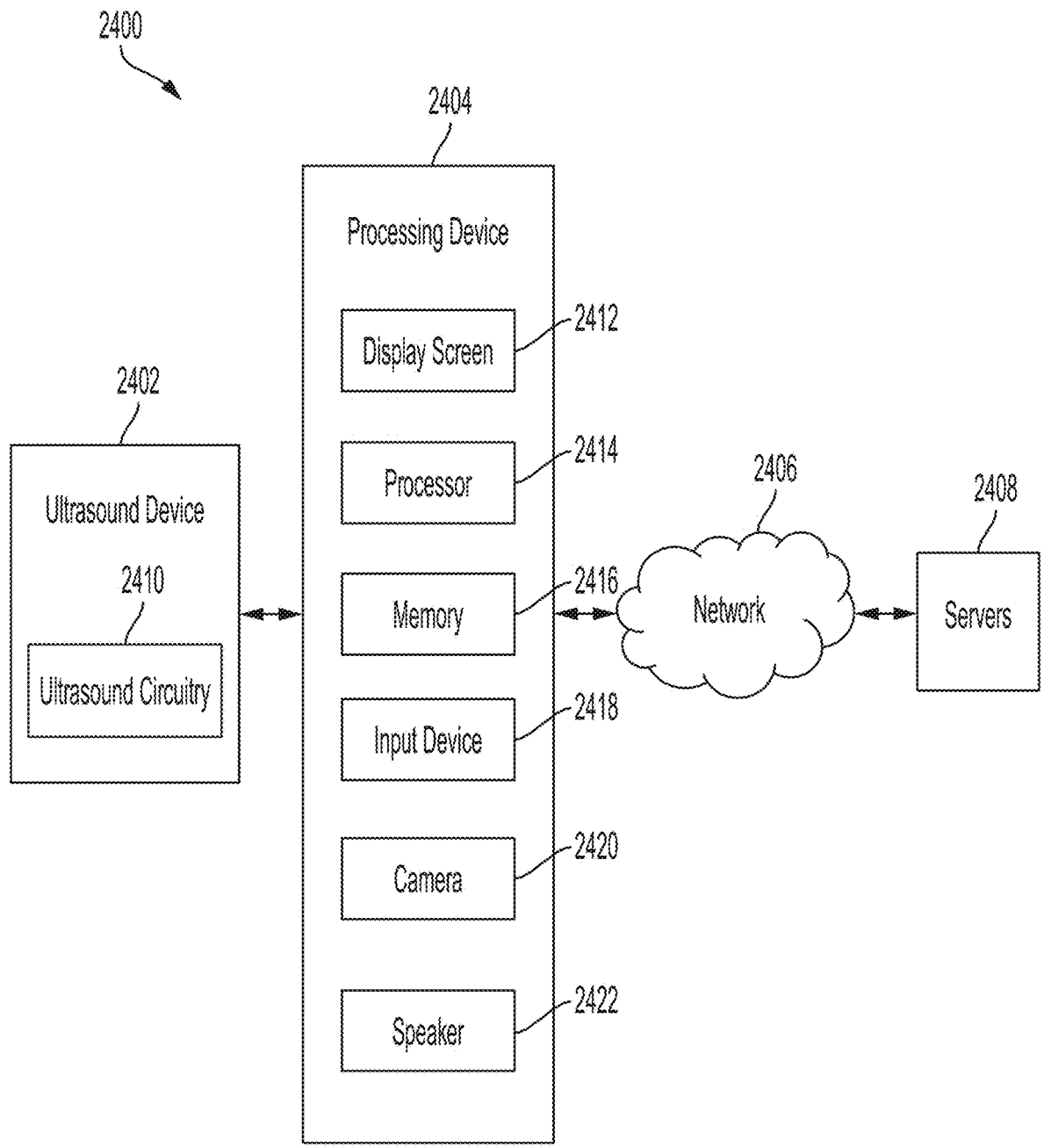
FIG. 24 illustrates a schematic block diagram of an example ultrasound system, in accordance with certain embodiments described herein.

FIG. 24 illustrates a schematic block diagram of an example ultrasound system 2400, in accordance with certain embodiments described herein. The ultrasound system 2400 includes an ultrasound device 2402 and a processing device 2404.

The ultrasound device 2402 includes ultrasound circuitry 2410. The processing device 2404 includes a display screen 2412, a processor 2414, a memory 2416, an input device 2418, a camera 2420, and a speaker 2422. The processing device 2404 is in wired (e.g., through a lightning connector or a mini-USB connector) and/or wireless communication (e.g., using BLUETOOTH, ZIGBEE, and/or WiFi wireless protocols) with the ultrasound device 2402.

The ultrasound device 2402 may be configured to generate ultrasound data that may be employed to generate an ultrasound image. The ultrasound device 2402 may be constructed in any of a variety of ways. In some embodiments, the ultrasound device 2402 includes a transmitter that transmits a signal to a transmit beamformer which in turn drives transducer elements within a transducer array to emit pulsed ultrasonic signals into a structure, such as a patient. The pulsed ultrasonic signals may be back-scattered from structures in the body, such as blood cells or muscular tissue, to produce echoes that return to the transducer elements. These echoes may then be converted into electrical signals by the transducer elements and the electrical signals are received by a receiver. The electrical signals representing the received echoes are sent to a receive beamformer that outputs ultrasound data. The ultrasound circuitry 2410 may be configured to generate the ultrasound data. The ultrasound circuitry 2410 may include one or more ultrasonic transducers monolithically integrated onto a single semiconductor die. The ultrasonic transducers may include, for example, one or more capacitive micromachined ultrasonic transducers (CMUTs), one or more CMOS (complementary metal-oxide-semiconductor) ultrasonic transducers (CUTs), one or more piezoelectric micromachined ultrasonic transducers (PMUTs), and/or one or more other suitable ultrasonic transducer cells. In some embodiments, the ultrasonic transducers may be formed on the same chip as other electronic components in the ultrasound circuitry 2410 (e.g., transmit circuitry, receive circuitry, control circuitry, power management circuitry, and processing circuitry) to form a monolithic ultrasound device. The ultrasound device 2402 may transmit ultrasound data and/or ultrasound images to the processing device 2404 over a wired (e.g., through a lightning connector or a mini-USB connector) and/or wireless (e.g., using BLUETOOTH, ZIGBEE, and/or WiFi wireless protocols) communication link.

Referring now to the processing device 2404, the processor 2414 may include specially-programmed and/or special-purpose hardware such as an application-specific integrated circuit (ASIC). For example, the processor 2414 may include one or more graphics processing units (GPUs) and/or one or more tensor processing units (TPUs). TPUs may be ASICs specifically designed for machine learning (e.g., deep learning). The TPUs may be employed, for example, to accelerate the inference phase of a neural network. The processing device 2404 may be configured to process the ultrasound data received from the ultrasound device 2402 to generate ultrasound images for display on the display screen 2412. The processing may be performed by, for example, the processor 2414. The processor 2414 may also be adapted to control the acquisition of ultrasound data with the ultrasound device 2402. The ultrasound data may be processed in real-time during a scanning session as the echo signals are received. In some embodiments, the displayed ultrasound image may be updated a rate of at least 5 Hz, at least 10 Hz, at least 20 Hz, at a rate between 5 and 60 Hz, at a rate of more than 20 Hz. For example, ultrasound data may be acquired even as images are being generated based on previously acquired data and while a live ultrasound image is being displayed. As additional ultrasound data is acquired, additional frames or images generated from more-recently acquired ultrasound data are sequentially displayed. Additionally, or alternatively, the ultrasound data may be stored temporarily in a buffer during a scanning session and processed in less than real-time.

The processing device 2404 may be configured to perform certain of the processes (e.g., the process 2300) described herein using the processor 2414 (e.g., one or more computer hardware processors) and one or more articles of manufacture that include non-transitory computer-readable storage media such as the memory 2416. The processor 2414 may control writing data to and reading data from the memory 2416 in any suitable manner. To perform certain of the processes described herein, the processor 2414 may execute one or more processor-executable instructions stored in one or more non-transitory computer-readable storage media (e.g., the memory 2416), which may serve as non-transitory computer-readable storage media storing processor-executable instructions for execution by the processor 2414. The camera 2420 may be configured to detect light (e.g., visible light) to form an image. The camera 2420 may be on the same face of the processing device 2404 as the display screen 2412. The display screen 2412 may be configured to display images and/or videos, and may be, for example, a liquid crystal display (LCD), a plasma display, and/or an organic light emitting diode (OLED) display on the processing device 2404. The input device 2418 may include one or more devices capable of receiving input from a user and transmitting the input to the processor 2414. For example, the input device 2418 may include a keyboard, a mouse, a microphone, touch-enabled sensors on the display screen 2412, and/or a microphone. The display screen 2412, the input device 2418, the camera 2420, and the speaker 2422 may be communicatively coupled to the processor 2414 and/or under the control of the processor 2414.

It should be appreciated that the processing device 2404 may be implemented in any of a variety of ways. For example, the processing device 2404 may be implemented as a handheld device such as a mobile smartphone or a tablet. Thereby, a user of the ultrasound device 2402 may be able to operate the ultrasound device 2402 with one hand and hold the processing device 2404 with another hand. In other examples, the processing device 2404 may be implemented as a portable device that is not a handheld device, such as a laptop. In yet other examples, the processing device 2404 may be implemented as a stationary device such as a desktop computer. The processing device 2404 may be connected to the network 2406 over a wired connection (e.g., via an Ethernet cable) and/or a wireless connection (e.g., over a WiFi network). The processing device 2404 may thereby communicate with (e.g., transmit data to or receive data from) the one or more servers 2408 over the network 2406. For example, a party may provide from the server 2408 to the processing device 2404 processor-executable instructions for storing in one or more non-transitory computer-readable storage media which, when executed, may cause the processing device 2404 to perform certain of the processes (e.g., the process 2300) described herein. For further description of ultrasound devices and systems, see U.S. patent application Ser. No. 15/415,434 titled "UNIVERSAL ULTRASOUND DEVICE AND RELATED APPARATUS AND METHODS," filed on Jan. 25, 2017 and published as U.S. Pat. App. Publication No. 2017-0360397 A1 (and assigned to the assignee of the instant application).

FIG. 24 should be understood to be non-limiting. For example, the ultrasound system 2400 may include fewer or more components than shown and the processing device 2404 and ultrasound device 2402 may include fewer or more components than shown. In some embodiments, the processing device 2404 may be part of the ultrasound device 2402.

Various aspects of the present disclosure may be used alone, in combination, or in a variety of arrangements not specifically described in the embodiments described in the foregoing and is therefore not limited in its application to the details and arrangement of components set forth in the foregoing description or illustrated in the drawings. For example, aspects described in one embodiment may be combined in any manner with aspects described in other embodiments.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

As used herein, reference to a numerical value being between two endpoints should be understood to encompass the situation in which the numerical value can assume either of the endpoints. For example, stating that a characteristic has a value between A and B, or between approximately A and B, should be understood to mean that the indicated range is inclusive of the endpoints A and B unless otherwise noted.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

What is claimed is:

1. An apparatus, comprising:
    a processing device in operative communication with an ultrasound device, the processing device configured to:
        display an initial ultrasound image collected by the ultrasound device;
        configure the ultrasound device to perform a three-dimensional ultrasound imaging sweep based on the initial ultrasound image collected by the ultrasound device, wherein the three-dimensional ultrasound imaging sweep comprises an elevational sweep of a bladder;
        display ultrasound images as the ultrasound images are collected during the three-dimensional ultrasound imaging sweep;
        display a cine including ultrasound images that were collected during the three-dimensional ultrasound imaging sweep, wherein at least a subset of the ultrasound images are each displayed in the cine with a respective indicator overlaid thereon, wherein the respective indicator for each ultrasound image in the subset indicates a segmented portion of the ultrasound image, wherein the segmented portion indicates an anatomical structure in the ultrasound image; and
        display a three-dimensional visualization based at least on the segmented portions of the subset of the ultrasound images that were collected during the three-dimensional ultrasound imaging sweep, wherein the three-dimensional visualization comprises a three-dimensional visualization of a volume of the bladder depicted in the ultrasound images, and wherein the segmented portions of the ultrasound images comprise interiors of the bladder.

2. The apparatus of claim 1, wherein the ultrasound device is configured to perform the three-dimensional ultrasound imaging sweep while a user maintains the ultrasound device at approximately a same position and orientation at which the ultrasound device collected the initial ultrasound image.

3. The apparatus of claim 1, wherein the ultrasound device is configured to use a two-dimensional array of ultrasound transducers on a chip to perform beamforming in order to perform the three-dimensional ultrasound imaging sweep.

4. The apparatus of claim 1, wherein the processing device is configured, when displaying the ultrasound images as the ultrasound images are collected during the three-dimensional ultrasound imaging sweep, to display a most recently collected ultrasound image.

5. The apparatus of claim 1, wherein the processing device is configured, when displaying the ultrasound images as the ultrasound images are collected during the three-dimensional ultrasound imaging sweep, to display the ultrasound images in real-time.

6. The apparatus of claim 1, wherein the processing device is further configured to use a statistical model to generate the segmented portions of the ultrasound images.

7. The apparatus of claim 1, wherein the three-dimensional visualization comprises a three-dimensional visualization of a bladder.

8. The apparatus of claim 1, wherein the processing device is configured, when displaying the three-dimensional visualization, to display an orientation indicator that indicates a position of the ultrasound device relative to a bladder depicted by the three-dimensional visualization.

9. The apparatus of claim 1, wherein the processing device is configured, when displaying the three-dimensional visualization, to display an orientation indicator that indicates a position of a bottom plane of the ultrasound images collected during the three-dimensional ultrasound imaging sweep relative to a bladder depicted by the three-dimensional visualization.

10. The apparatus of claim 1, wherein the processing device is further configured to:
    detect a dragging movement and/or a pinching movement across a touch-sensitive display screen of the processing device; and
    based on the dragging movement and/or the pinching movement, display the three-dimensional visualization as if the three-dimensional visualization were being rotated and/or zoomed in three dimensions.

11. The apparatus of claim 1, wherein the processing device is further configured to perform a measurement based on the segmented portions of the ultrasound images collected during the three-dimensional ultrasound imaging sweep.

12. The apparatus of claim 11, wherein the measurement comprises a measurement of a volume of a bladder.

13. The apparatus of claim 1, wherein the segmented portions of the ultrasound images comprise interiors of a bladder depicted in the ultrasound images.

14. The apparatus of claim 1, wherein an imaging slice of the initial ultrasound image comprises a center imaging slice of the three-dimensional ultrasound imaging sweep.

15. The apparatus of claim 1, wherein an imaging slice of the initial ultrasound image comprises an extreme of the three-dimensional ultrasound imaging sweep.

16. The apparatus of claim 1, wherein the processing device is further configured to display the segmented portions of the ultrasound images as the ultrasound images are collected during the three-dimensional ultrasound imaging sweep.

17. The apparatus of claim 1, wherein the processing device comprises a handheld processing device.

* * * * *